US012648952B2

(12) United States Patent
Deisher et al.

(10) Patent No.: US 12,648,952 B2
(45) Date of Patent: Jun. 9, 2026

(54) METHODS OF TREATMENT USING ICAM-MODULATING AGENTS

(71) Applicant: AVM Biotechnology, LLC, Seattle, WA (US)

(72) Inventors: Theresa Deisher, Seattle, WA (US); Scot Wayne McKay, Seattle, WA (US)

(73) Assignee: AVM Biotechnology, LLC, Seattle, WA (US)

( * ) Notice: Subject to any disclaimer, the term of this patent is extended or adjusted under 35 U.S.C. 154(b) by 693 days.

(21) Appl. No.: 17/927,919

(22) PCT Filed: Jun. 1, 2021

(86) PCT No.: PCT/US2021/035108
§ 371 (c)(1),
(2) Date: Nov. 28, 2022

(87) PCT Pub. No.: WO2021/247473
PCT Pub. Date: Dec. 9, 2021

(65) Prior Publication Data
US 2023/0210868 A1 Jul. 6, 2023

(30) Foreign Application Priority Data
Jun. 1, 2020 (WO) ................ PCT/US2020/035524

(51) Int. Cl.
*A61K 31/573* (2006.01)
*A61P 35/00* (2006.01)

(52) U.S. Cl.
CPC ............ *A61K 31/573* (2013.01); *A61P 35/00* (2018.01)

(58) Field of Classification Search
CPC .............................. A61K 31/573; A61P 35/00
See application file for complete search history.

(56) References Cited

U.S. PATENT DOCUMENTS

| | | |
|---|---|---|
| 9,512,200 B2 | 12/2016 | Deisher |
| 9,962,408 B2 | 5/2018 | Deisher |
| 10,030,230 B2 | 7/2018 | Deisher |
| 10,426,740 B1 | 10/2019 | Deisher |
| 2018/0296572 A1 | 10/2018 | Deisher |
| 2020/0108078 A1 | 4/2020 | Deisher |
| 2020/0289650 A1 | 9/2020 | Deisher et al. |
| 2022/0160729 A1 | 5/2022 | Deisher |
| 2023/0172950 A1 | 6/2023 | Deisher et al. |

FOREIGN PATENT DOCUMENTS

| | | |
|---|---|---|
| EP | 3488851 A1 | 5/2019 |
| WO | 2020263830 A1 | 12/2020 |

OTHER PUBLICATIONS

AVM Biotechnology brochure, "AVM0703 Lympho- and Mono-ablation for relapsed/refractory lymphocytic blood cancers, immune reset for autoimmune disease, and replacement of chemotherapy/radiation preconditioning before CarT or cell therapy," Jun. 1, 2019 (ASCO meeting), 6 pages.
AVM Biotechnology slides, "Revolutionizing the Future of Immunotherapy," Jun. 19, 2019, 10 pages.
Deisher et al., "AVM0703, a New Treatment Option for Lymphoma Patients," Blood, vol. 134, No. Suppl. 1. (2019), p. 5308.
Dobos et al., "Glucocorticoid Receptor Expression and Antiprolifera-tive Effect of Dexamethasone on Human Melanoma Cells," Pathol. Oncol. Res. 17:729-734 (2011).
International Search Report and Written Opinion issued in Interna-tional Application No. PCT/US2020/035524, mailed Feb. 4, 2021, 11 pages.
International Search Report and Written Opinion issued in Interna-tional Application No. PCT/US2021/035108, mailed Sep. 29, 2021, 8 pages.
Kessel et al. "Ligation of intercellular adhesion molecule 3 induces apoptosis of human blood eosinophils and neutrophils," Journal of Allergy and Clinical Immunology 118(4):831-836 (2006).
Kudawara et al., "In vivo inhibition of tumour growth by dexamethasone in murine osteosarcomas," European Journal of Cancer 37:1703-1708 (2001).
Martinez-Caceres et al. "Stimulation through CD50 (ICAM-3) induces both activation and programmed cell death of human thymocytes," Tissue Antigens 48(6):626-635 (1996).
Morgan et al., "Distinct Effects of Dexamethasone on Human Natural Killer Cell Responses Dependent on Cytokines," Front. Immunol. 8(432):1-15 (2017).

*Primary Examiner* — Kamal A Saeed
*Assistant Examiner* — Quincy McKoy
(74) *Attorney, Agent, or Firm* — McNeill PLLC

(57) ABSTRACT

This invention pertains to methods of treating cancer and lymphocyte mediated diseases using Intercellular Adhesion Molecule (ICAM)-modulating agents.

17 Claims, 9 Drawing Sheets

FANTOM5 dataset

Scaled Tags Per Million

*Figure 2*

AVM0703 RECEPTOR RNA EXPRESSION ON PEDIATRIC CANCERS

Above 12.5 all are various leukemias or lymphomas

1976

Low expression on solid tumors
Some ALL also have low expression

1976 SAMPLES/1126 HEMATOLOGIC MALIGNANCIES/2 B-ALL CNVS/1 T-ALL CNV/1 B-ALL SNP

Dexamethasone base doses that induced apoptosis include 50, 100, 175, and 250 μM.

Splenocytes Live/Dead 4hr

% Dead
% Alive
% Apoptosis
Debris

Dexa Induced Apoptosis Decreases above 100 micromole

In vitro      In vivo
750 uM = 21 mg/kg
500 uM = 14 mg/kg
250 uM =  7 mg/kg
100 uM = 2.8 mg/kg

METHODS OF TREATMENT USING ICAM-MODULATING AGENTS

CROSS-REFERENCE TO RELATED APPLICATION

This application is a national phase entry pursuant to 35 U.S.C. § 371 of International Application No. PCT/US2021/035108, filed Jun. 1, 2021, which claims the benefit of priority of International Application No. PCT/US2020/35524, filed Jun. 1, 2020, each of which is incorporated by reference herein in its entirety for any purpose.

FIELD

This disclosure pertains to methods of treating cancer and lymphocyte mediated diseases using Intercellular Adhesion Molecule (ICAM)-modulating agents. More specifically, the disclosure pertains to methods of treating cancer using high dose glucocorticoids such as dexamethasone.

BACKGROUND

Reducing cytotoxic chemotherapy use is a top priority goal of the National Cancer Institute. Chimeric antigen receptor (CAR) T-cell therapy has shown remarkable success in the treatment of CD-19-expressing B-cell acute lymphocytic leukemia. However, there are a number of obstacles that limit CAR T-cell therapy for solid tumors: ineffective trafficking to the tumor as well immunosuppressive microenvironments in solid tumors limit T-cell efficacy. In addition, CAR T therapies have been associated with serious adverse effects, including cytokine release syndrome (CRS), neuroedema, and graft versus host disease (GvHD).

Despite efforts to reduce the toxicities associated with cancer treatments, the physical toll and medical costs to manage these toxicities remain a significant concern. For example, up to 41% of blood cancer patients choose to stop taking the new kinase/proteasome inhibitors or biologics due to the physical and financial toxicities associated with these drugs (Mato 2018, Kadri 2017, Mato 2016 and Barrett 2010, each of which is hereby incorporated by reference in its entirety).

Adhesion molecules are glycoproteins expressed on cell surfaces, which mediate the contact between two cells (both homotypic and heterotypic interactions) or between cells and the extracellular matrix (Hua 2013, which is hereby incorporated by reference in its entirety). ICAMs are type I transmembrane glycoproteins of the immunoglobulin superfamily, which are ligands for antigens expressed on the surface of immune cells, such as leukocyte integrins. The five known ICAM family members (ICAM1-ICAM5) are known to play a role in inflammation, immune responses, and intracellular signalling (Shen et al 2018 which is hereby incorporated by reference in its entirety).

Of the five ICAMs identified, ICAM-1 (Intercellular Adhesion Molecule 1; also known as CD54) is the most extensively studied (Hua et al, 2013). ICAM-1 is expressed on many cell types including endothelial cells and different cancer cell entities. Experimental data indicate that ICAM-1 can activate intracellular signaling pathways in cancer cells leading to enhanced cell motility, invasion and metastasis (Schroder at el 2011 which is hereby incorporated by reference in its entirety).

ICAM-3 (also known as CD50) is expressed by lymphocytes, monocytes, eosinophils and neutrophils (as well as on bronchioles, and by lymphoma cells and some melanoma, sarcoma, and other cancer cells). Information on the underlying ICAM3 gene is available online, for instance on the Ensemble database; see entry ENSG00000076662. ICAM3-mediated signaling proceeds via recruitment of Src by the YLPL motif in the ICAM3 intracellular domain leading to PI3K-AKT phosphorylation cascades (Shen et al, 2018). ICAM3 is one of the most heavily Asp-glycosylated proteins in the human body. Asparagine residues (Asp) become decorated with glycans linked at the nitrogen of the amide side group. This is a biologically important posttranslational modification that begins in the endoplasmic reticulum with the transfer of a core glycan comprising three mannose subunits.

Shen et al (2018) have reported ICAM3 involvement in cancer cell stemness in vitro and in vivo. ICAM3 expression on eosinophils is decreased by exposure to modest concentrations of dexamethasone (100 pM to 1 µM) (Juan et al, 1999, which is hereby incorporated by reference in its entirety). Glycosylation of ICAM3 can be reduced when cells are used ex vivo or on in vitro cell lines, resulting in disparate in vivo versus ex vivo or in vitro effects of ICAM3 activation or inhibition.

ICAM4 was originally named the 'LW glycoprotein' and its expression was thought to be largely restricted to red blood cells, although more recent studies have shown it to be expressed also by macrophages (Choi et al, 2017, which is hereby incorporated by reference in its entirety). Information on the underlying ICAM4 gene is available online, for instance on the Ensemble database; see entry ENSG00000105371.

The present authors have previously found that high concentrations of glucocorticoids could be used to condition patients to enhance the efficacy of cellular immunotherapies such as adoptive T cell therapy; described in International patent application PCT/US2018/025517 (published as WO2018/183927). In that application, the authors noted the toxicities associated with chemotherapy and radiation mediated preconditioning, which is believed to non-selectively destroy the cellularity of the spleen. The authors provided glucocorticoids (a subclass of steroids) and other non-toxic lymphodepleting agents, at acute doses, to benefit cancer patients who receive cellular immunotherapies.

In international patent application PCT/US2019/054395 the present authors have also described the use of high concentrations of glucocorticoids to cause lymphodepletion of peripheral blood lymphocytes without substantially affecting the cell count of other cells. In that application, the authors reported that high concentrations of glucocorticoids can deplete peripheral blood lymphocytes including, for example, islet-specific autoreactive T-cells responsible for diabetes autoimmunity, but spares neutrophils, platelets, RBCs and stem cells (both HSCs and MSCs). The authors provided glucocorticoids as a non-myeloablative regimen that can perform a safe immunologic reset with efficacy comparable to chemotherapy.

A need exists for further treatments for cancer that are safer and associated with fewer toxicities and/or greater efficacy than currently available therapies. Treatments that are simpler, less toxic, and less costly are desired.

SUMMARY

The present disclosure is based on the surprising finding that, following high dose administration, glucocorticoid molecules can bind and block intercellular adhesion molecules such as ICAM3. The binding is cooperative and up to 26 molecules bind the first Ig domain of ICAM3. When administered at high doses, glucocorticoids may be 'soaked up' by ICAM3, which is expressed at substantial levels on cells such as lymphocytes, monocytes and neutrophils, as well as on cancer cell types such as melanoma and osteosarcoma and bronchiole cells, which can result in concentration-dependent apoptosis of these ICAM3 expressing cells (see Examples 1 and 2). The authors have also demonstrated that at ex vivo or in vitro concentrations equal to the peak blood concentrations of HED of 7-15 mg/kg dexamethasone phosphate or greater that there is no direct apoptotic effect on mouse or human whole blood or mouse splenocytes, demonstrating that glucocorticoid receptors are not bound/activated at these high concentrations.

Without being bound by theory, the authors believe that binding of glucocorticoids such as dexamethasone to ICAM3 expressed on splenocytes and/or thymocytes and/or bone marrow resident immune cells can lead to the production and mobilization of novel immune cell populations, including novel populations of Natural Killer T (NKT) cells, from the spleen, thymus, or bone marrow into the circulation. These novel NKT cells can identify and target cells for destruction. Binding of suprapharmacologic doses of dexamethasone to ICAM3 expressed on peripheral blood immune cells could present the dexamethasone to spleen, thymus and/or bone marrow immune cells to trigger the induction and mobilization of the novel immune populations in to the blood.

Without being bound by theory, the authors also believe that the binding of dexamethasone or its metabolites to the Ig1 domain of ICAM3 could lead to activation of ICAM3 similar to reported agonistic antibodies that bind to the same region, or could lead to shedding of ICAM3 as reported in Juan et al, 1999. Either activation of ICAM3 signalling or shedding of ICAM3 from the cell surface could trigger the production and ultimate mobilization into the peripheral blood the novel immune cell populations observed after suprapharmacologic dexamethasone or betamethasone dosing. Glucocorticoid binding to ICAM3 may also lead to the cell becoming marked for attack by lymphocytes such as NKT cells and CD8+ T cells. ICAM3 shedding may also occur following glucocorticoid binding, further stimulating an immune response against these cell types.

Accordingly, in a first aspect, the disclosure provides a method of treating cancer or a lymphocyte-mediated disease or a microbial disease in a subject, the method comprising administering a therapeutically effective amount of a glucocorticoid to the subject, wherein the glucocorticoid induces cell death of ICAM3 expressing cells by binding to ICAM3.

In some embodiments, the glucocorticoid is selected from the group consisting of: dexamethasone, hydrocortisone, methylprednisolone, prednisone, prednisolone, prednylidene, cortisone, budesonide, betamethasone, flumethasone, ciclesonide, and beclomethasone. In some preferred embodiments, the glucocorticoid is selected from the group consisting of: dexamethasone, betamethasone, and methylprednisone, preferably wherein the glucocorticoid is dexamethasone or betamethasone.

In some embodiments, the glucocorticoid is selected from the group consisting of dexamethasone base, dexamethasone sodium phosphate, dexamethasone hemisuccinate, dexamethasone sodium succinate, dexamethasone succinate, dexamethasone isonicotinate, dexamethasone-21-acetate, dexamethasone phosphate, dexamethasone-21-phosphate, dexamethasone tebutate, dexamethasone-17-valerate, dexamethasone acetate monohydrate, dexamethasone pivalate, dexamethasone palmitate, dexamethasone-21-palmitate, dexamethasone dipropionate, dexamethasone propionate, dexamethasone acetate anhydrous, dexamethasone-21-phenylpropionate, dexamethasone-21-sulfobenzoate, dexamethasone hemo-sulfate, dexamethasone sulfate, dexamethasone beloxil, dexamethasone acid, dexamethasone acefurate, dexamethasone carboximide, dexamethasone cipecilate, dexamethasone 21-phosphate disodium salt, dexamethasone mesylate, dexamethasone linoleate, dexamethasone glucoside, dexamethasone glucuronide, dexamethasone iodoacetate, dexamethasone oxetanone, carboxymethylthio-dexamethasone, dexamethasonebisethoximes, dexamethasone epoxide, dexamethasonelinolelaidate, dexamethasone methylorthovalerate, dexamethasone spermine, 6-hydroxy dexamethasone, dexamethasone tributyacetate, dexamethasone aspartic acid, dexamethasone galactopyranose, dexamethasone hydrochloride, hydroxy dexamethasone, carboxy dexamethasone, desoxy dexamethasone, dexamethasone butazone, dexamethasone cyclodextrin, dihydro dexamethasone, oxo dexamethasone, propionyloxy dexamethasone, dexamethasone galactodie, dexamethasone isonicotinate, dexamethasone sodium hydrogen phosphate, dexamethasone aldehyde, dexamethasone pivlate, dexamethasone tridecylate, dexamethasone crotonate, dexamethasone methanesulfonate, dexamethasone butylacetate, dehydro dexamethasone, dexamethasone Isothiocyanatoethyl)Thioether, dexamethasone bromoacetate, dexamethasone hemiglutarate, deoxy dexamethasone, dexamethasone chlorambucilate, dexamethasone melphalanate, formyloxy dexamethasone, dexamethasone butyrate, dexamethasone laurate, dexamethasone acetate, and any combination treatment that contains a form of dexamethasone. In some preferred embodiments, the dexamethasone is dexamethasone base or dexamethasone sodium phosphate.

In some embodiments, the glucocorticoid is administered to the subject at a dose equivalent to about: at least 6 mg/kg human equivalent dose (HED) of dexamethasone base; at least 12 mg/kg human equivalent dose (HED) of dexamethasone base; at least 15 mg/kg human equivalent dose (HED) of dexamethasone base; at least 18 mg/kg human equivalent dose (HED) of dexamethasone base; at least 24 mg/kg human equivalent dose (HED) of dexamethasone base; 15 mg/kg human equivalent dose (HED) of dexamethasone base; 18 mg/kg human equivalent dose (HED) of dexamethasone base; 24 mg/kg human equivalent dose (HED) of dexamethasone base; 30 mg/kg human equivalent dose (HED) of dexamethasone base; 45 mg/kg human equivalent dose (HED) of dexamethasone base; at least 6-12 mg/kg human equivalent dose (HED) of dexamethasone base; or, at a human equivalent dose (HED) of dexamethasone base taking a value in mg/kg from a range of mg/kg values, wherein said range is bound by two of the mg/kg values set forth above.

In some embodiments, the glucocorticoid is administered as a single acute dose, or as a total dose given over about a 72 hour period. In some embodiments, the method comprises administering one or more further doses of a glucocorticoid to the subject, which may be administered: between 24 hours and 120 hours after a preceding administration; between 24 hours and 48 hours after a preceding administration; between 72 hours and 120 hours after a preceding administration; every 24, 48, 72, 96, 120, 144, or 168 hours after a first administration; once every two weeks after a first glucocorticoid administration; once monthly after a first administration; or twice weekly after a first administration.

In some embodiments, the subject is mammalian, preferably a human. In some embodiments, the subject has, is suspected of having, or has been diagnosed with cancer or a lymphocyte-mediated disease or a microbial disease.

In some embodiments, the lymphocyte-mediated disease is cancer. In some embodiments, the cancer is a lymphoma, melanoma, or osteosarcoma. In some preferred embodiments, the cancer is lymphoma, preferably a germinal cell lymphoma, B cell lymphoma, T cell lymphoma, or non-Hodgkin lymphoma.

In some embodiments, the lymphocyte-mediated disease is an allergic disease or autoimmune disease.

In some embodiments, the glucocorticoid induces apoptosis of ICAM3 expressing cells by binding to ICAM3. In some embodiments, the glucocorticoid causes ICAM3 shedding from the surface of a cell into the extracellular space. In some embodiments, the glucocorticoid causes ICAM3 expressing cells to be marked for attack by immune cells. In some embodiments, the glucocorticoid triggers or supports an effective immune response against an ICAM3 expressing cancer cell or lymphocyte.

The glucocorticoid may trigger or support an effective immune response by inducing and/or mobilising of a population of NKT cells that are characterized in that they express CD3, and:

i) express CD4, CD8, CD45, CD49b (CD56 in humans), CD62L, NK1.1, Ly6G, Sca1, and/or TCR gamma/delta; and/or ii) do not express: C-kit, B220, FoxP3, and/or TCR alpha/beta.

The population of NKT cells may not express: C-kit, B220, FoxP3, and/or TCR alpha/beta to any significant extent.

The glucocorticoid may trigger or support an effective immune response by inducing and/or mobilising a population of T cells that express CD3 to a very high level ("CD3-very-high"). The T cells may express both CD4 and CD8.

The glucocorticoid may trigger or support an effective immune response by inducing and/or mobilising a population of dendritic cells (DCs) that express CD11b to a very high level ("CD11b-very-high dendritic cells").

In a second aspect, the disclosure provides a glucocorticoid for use in a method according to the first aspect of the disclosure.

In a third aspect, the disclosure provides use of a glucocorticoid for the manufacture of a medicament for use in a method according to the first aspect of the disclosure.

The disclosure includes the combination of the aspects and preferred features described except where such a combination is clearly impermissible or expressly avoided

SUMMARY OF THE FIGURES

Embodiments and experiments illustrating the principles of the disclosure will now be discussed with reference to the accompanying figures in which.

6

Figure 2:
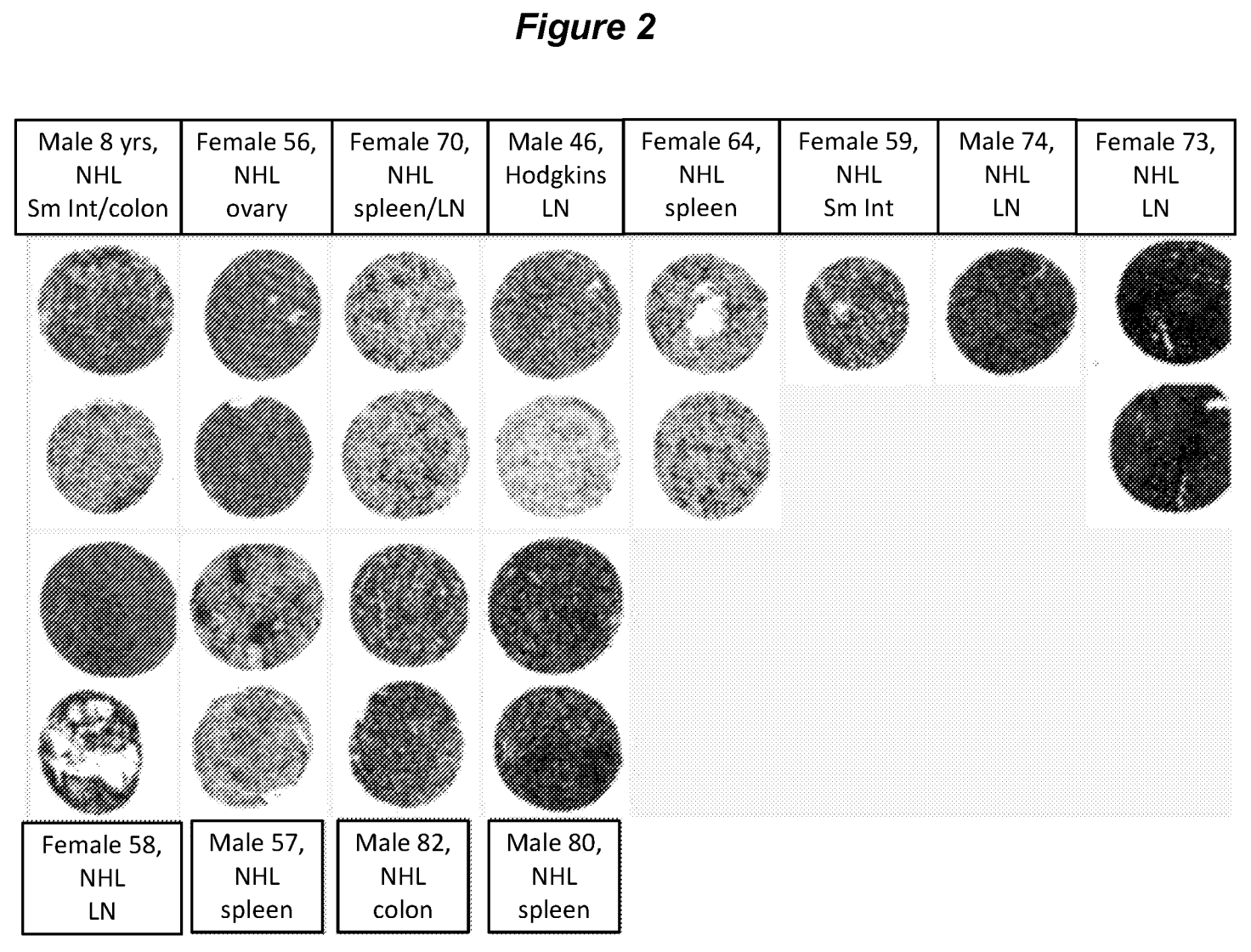

FIG. 2. The AVM0703 Receptor (ICAM3) is widely expressed by lymphomas; strong expression was identified on 12 out of 12 tested lymphoma biopsies. ICAM3 is also detected at low levels on some biopsied colorectal cancer cells, weakly on some breast cancer biopsies of duct carcinoma, and on bronchiole like cells from lung cancer biopsies but not on the cancerous cells (data not shown). Protein expression from biopsy samples is from the Human Proteome Project.

Figure 3:
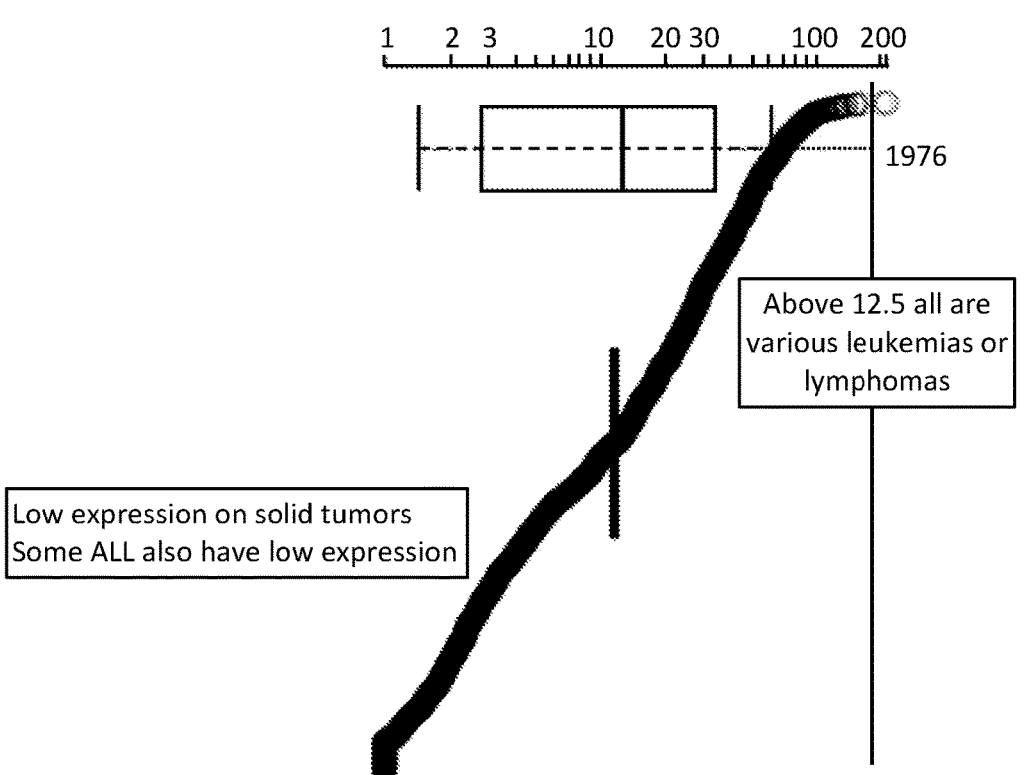

FIG. 3. The AVM0703 Receptor (ICAM3) is expressed on pediatric cancers (from St. Jude's Pediatric Cancer Genome Project). Cancers expressing ICAM3 mRNA levels above the median are all types of leukemias and lymphomas. There are some acute lymphocytic leukemia samples that express ICAM3 mRNA at levels below the median of all 1976 samples. All solid tumors had ICAM3 mRNA expression below the median.

Figure 4:
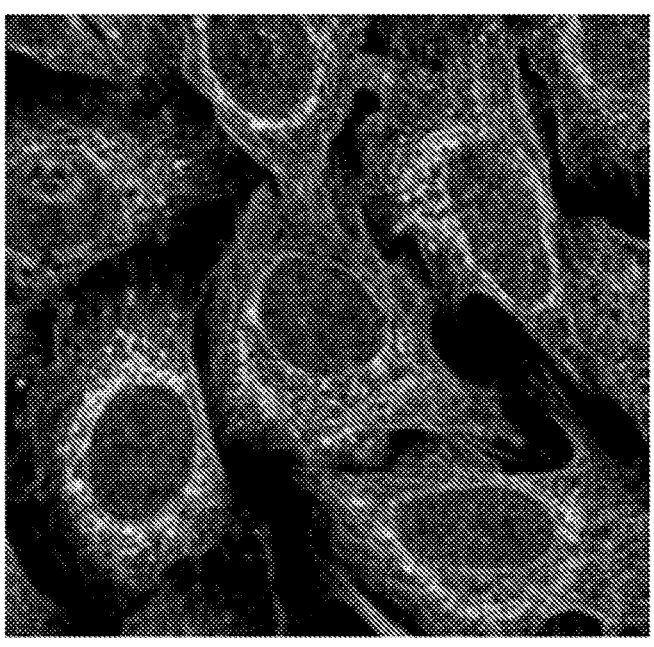

FIG. 4. The AVM0703 Receptor (ICAM3) is expressed by U2 OS osteosarcoma cells (from the Human Proteome Project).

Figure 5:
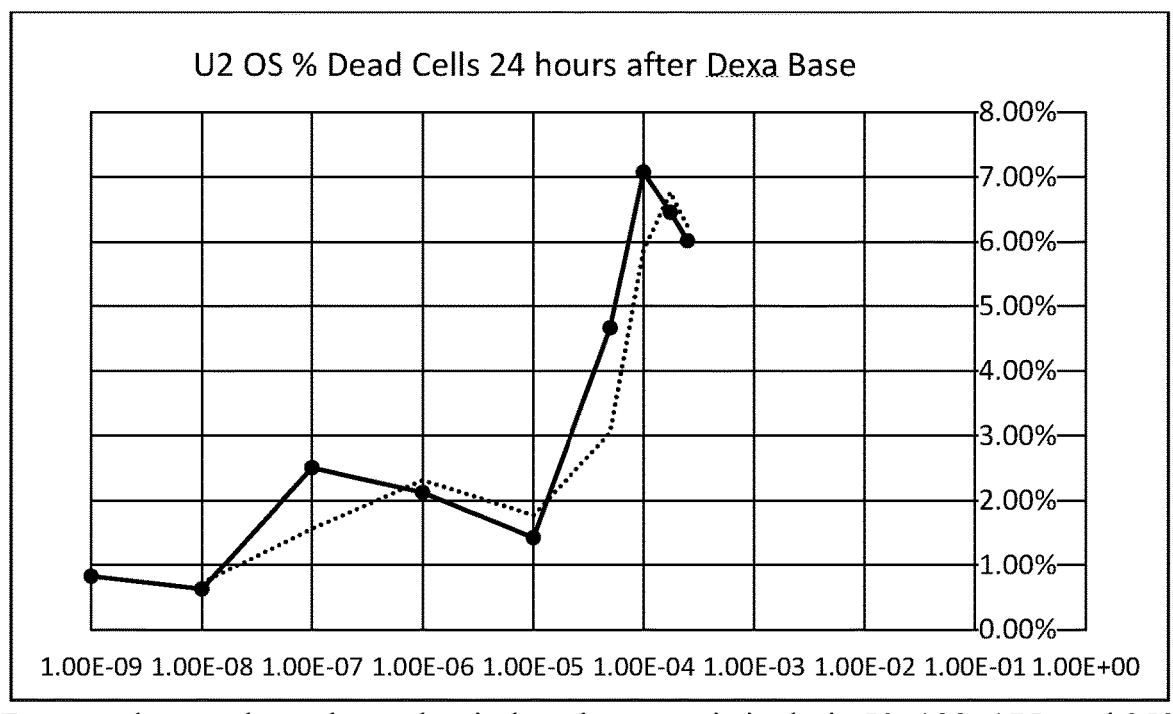

FIG. 5. PI staining of dead U2 osteosarcoma cells 24 hours after AVM0703 administration. AVM0703 induces in vitro apoptosis of U2 OS cells in a concentration-dependent manner. Dexamethasone base doses that induced apoptosis include 50, 100, 175, and 250 μM. U2 OS cells do not express the glucocorticoid receptor, demonstrating that activity is via activation/alteration of ICAM3.

Figure 6:
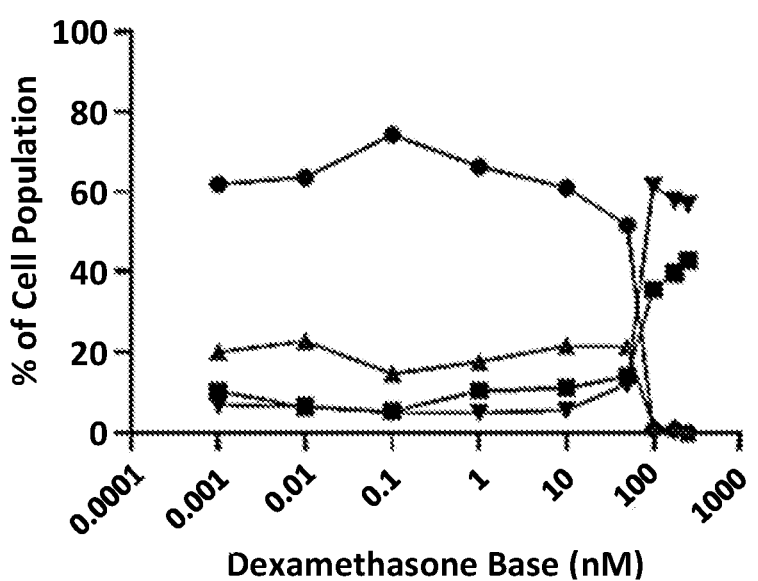
Figure 6:
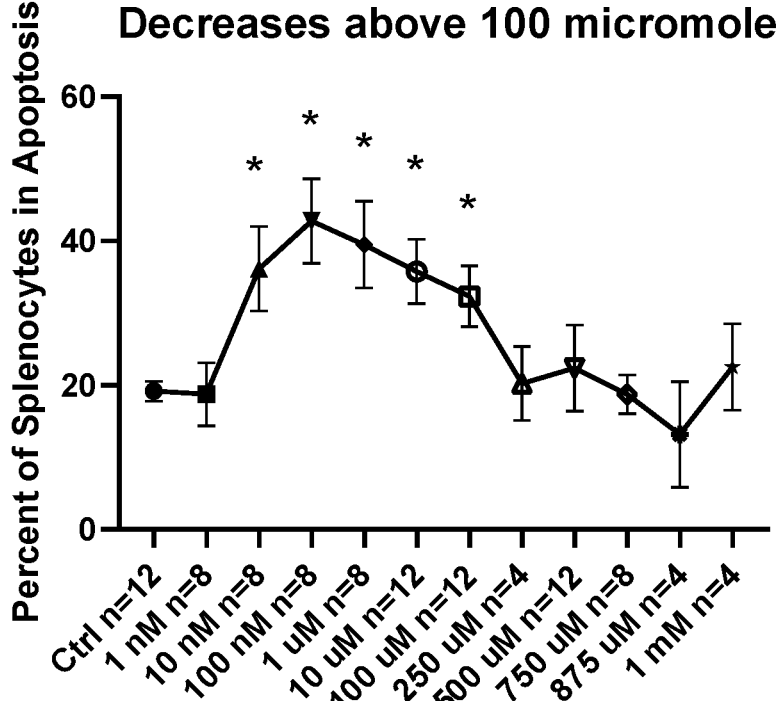

FIG. 6. Splenocyte viability following 4-6 hours incubation with dexamethasone base (1 nM-1 mM). FIG. 6 upper plot shows that at doses above 100 AVM0703 no longer induces apoptosis of freshly isolated splenocytes, demonstrating that ex vivo at concentrations equivalent to peak plasma concentrations following a human equivalent dose (HED) of 7 mg/kg or greater that glucocorticoid receptors are not bound or activated. FIG. 6 lower plot shows the same results in combined data from 3 separate experiments, with additional concentrations of AVM0703 tested. The expected glucocorticoid mediated splenocyte apoptosis was observed at concentrations between 10 nM to 100 μM.

Figure 7:
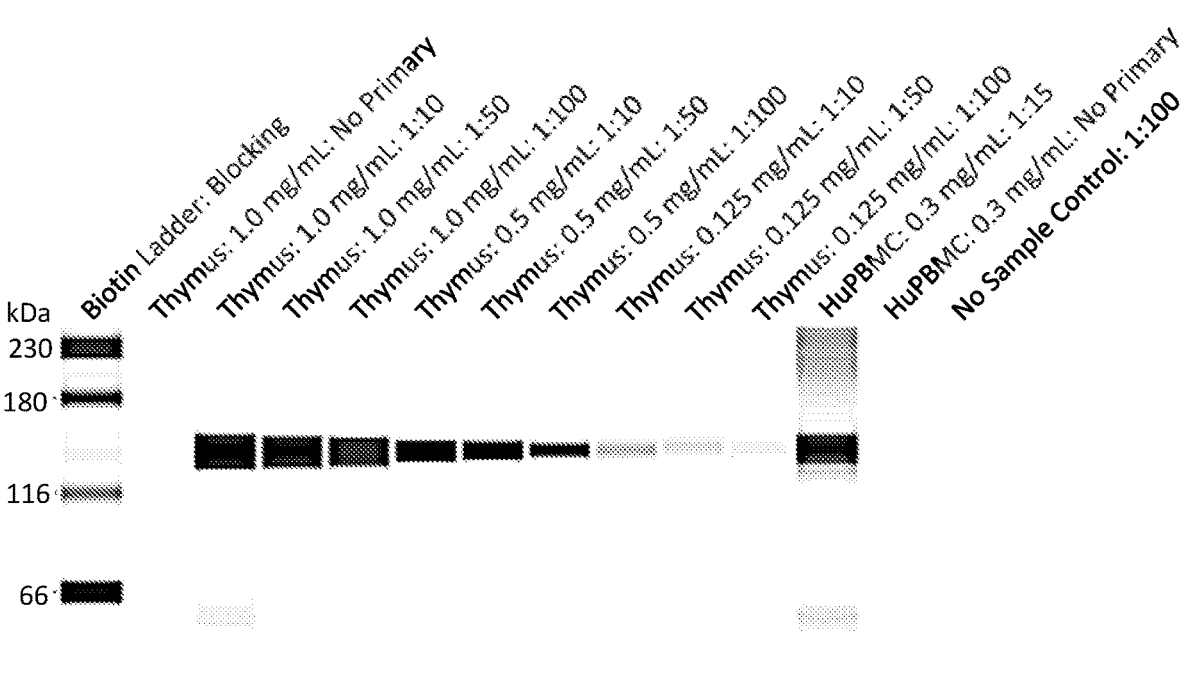

FIG. 7. Western blot detection of ICAM3 in C56BL/6 mouse thymus. In mouse thymus lysates a clear band is observed at 144 KDa, within the predicted molecular weight range for ICAM3. Human PBMCs show the same band at ~145 KDa along with a smaller band at 62 KDa.

Figure 8:
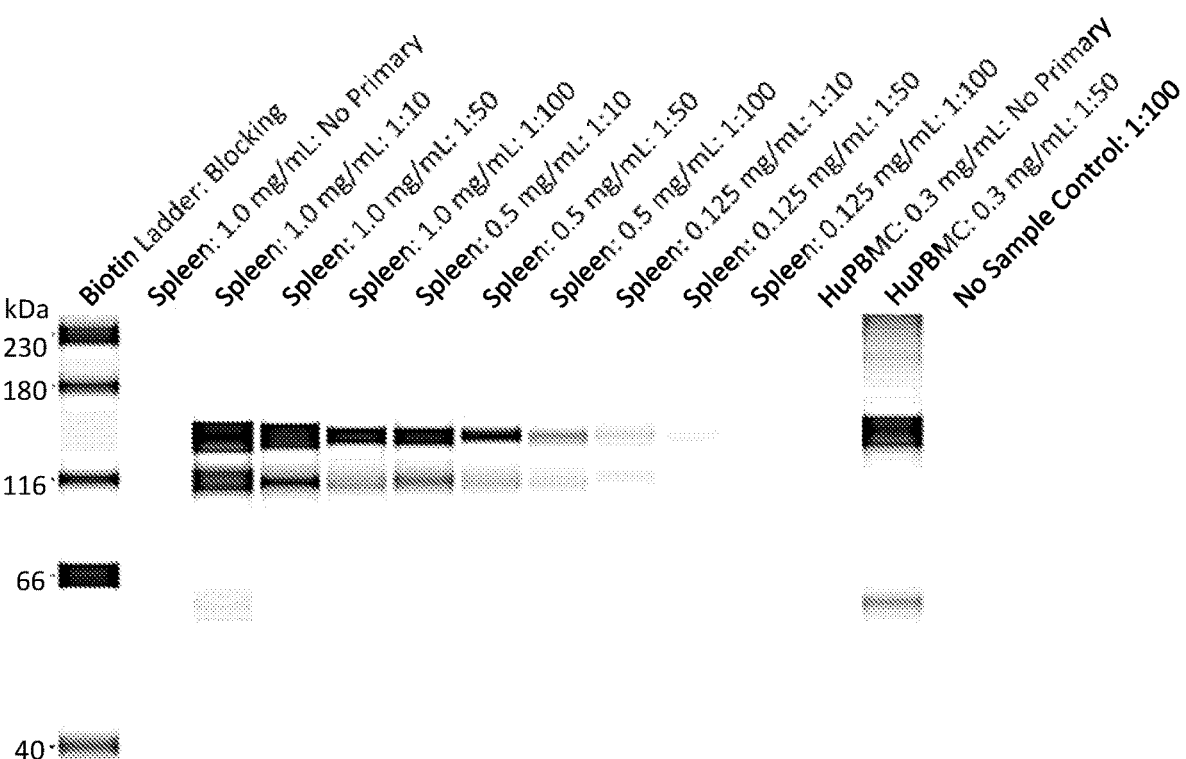

FIG. 8. Western blot detection of ICAM3 in C56BL/6 mouse spleen. In mouse spleen lysates 2 bands are observed at 145 KDa and 115 KDa. At the highest sample concentration and lowest primary antibody dilution, a much fainter band at ~62 KDa is also observed. The protein bands at 145 KDa and 62 KD are matched by those in the human PBMC positive control.

Figure 9:
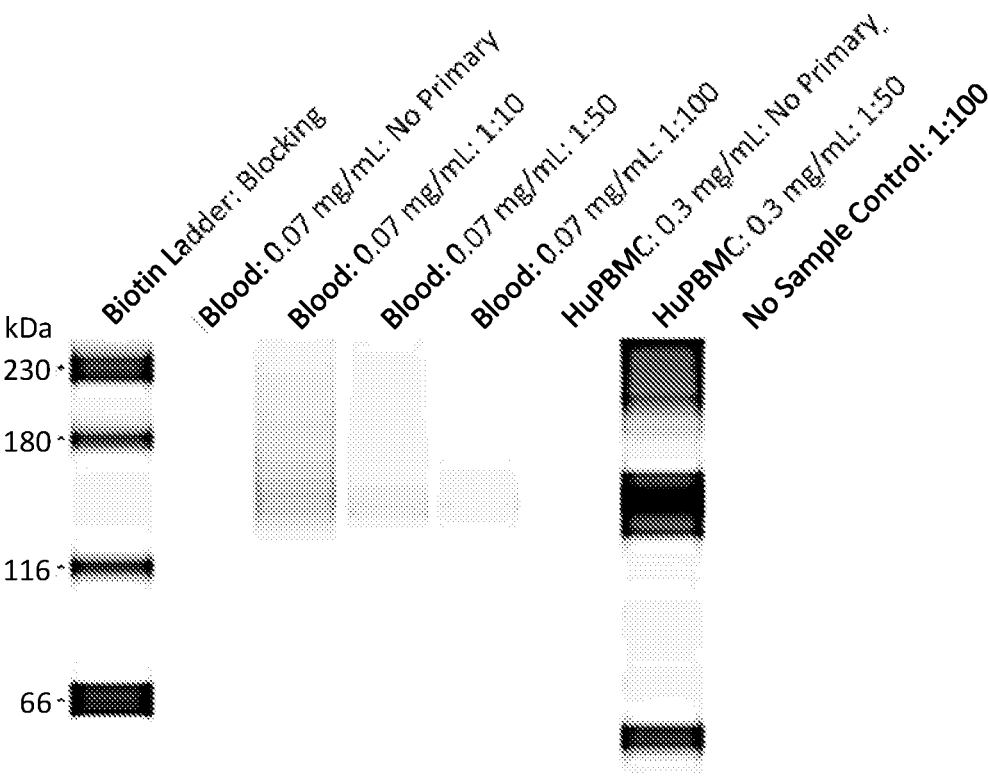

FIG. 9. Western blot detection of ICAM3 in C56BL/6 mouse blood. Experimental issues with the blood lysis resulted in lysates with very low concentration of protein. Nevertheless, at the lowest primary antibody dilution, a faint band is observed in mouse blood at ~149 KDa which matches the protein band size in the human PBMC positive control.

DETAILED DESCRIPTION

Aspects and embodiments of the present disclosure will now be discussed with reference to the accompanying figures. Further aspects and embodiments will be apparent to those skilled in the art. All documents mentioned in this text are incorporated herein by reference.

The present disclosure pertains to: methods of treating cancer or a lymphocyte-mediated disease or a microbial disease in a subject, the method comprising administering a therapeutically effective amount of an ICAM3 modulating agent to the subject. The present disclosure also provides ICAM3 modulating agents (which may be a glucocorticoid, such as dexamethasone) for use in such methods, as well as the use of an ICAM3 modulating agent (which may be a glucocorticoid, such as dexamethasone) for the manufacture of a medicament for use in such methods.

Pharmacological Action

A receptor antagonist is a ligand that binds to the receptor, thus occupying the receptor binding site, but without activating the receptor. In contrast, a receptor agonist binds and activates the receptor, which typically causes a signal to be transduced within the cell. Therefore, antagonists can exert biologically relevant actions by competing with agonists, and other receptor-binding agents, for binding. Antagonists are therefore commonly referred to as 'blockers'.

The glucocorticoid modulating agents of the present disclosure typically act as agonists on glucocorticoid receptors. However, the present application discloses the surprising capacity of glucocorticoid modulating agents (such as dexamethasone and other glucocorticoids) to bind the Intracellular Adhesion Molecule 3 (ICAM3) and induce cell death/apoptosis of ICAM3-expressing cells. Without being bound by theory, the authors believe that this apoptosis may be caused by one or more of: activation of ICAM3; triggering (activating) of cell apoptotic pathways; binding of ICAM3 leading to the cells being marked for attack by macrophages and/or leukocytes such as NKT cells and CD8+ T cells; and, shedding of ICAM3 from the cell surface.

ICAM-3 Modulating Agent

ICAM3 modulating agents in the context of the present disclosure are those which bind ICAM3 and promote the concentration dependent apoptotic cell death demonstrated in the Examples. Such ICAM3 modulating agents may promote said concentration dependent apoptotic cell death by inducing the production and mobilization of novel immune cells as outlined elsewhere herein. That is, without being bound by theory, such agents may bind ICAM3 and: block the signalling cascades caused by ICAM3 activation; activate signalling cascades to induce cell-mediated apoptosis; cause the ICAM3 expressing cell to become marked for attack by macrophages or lymphocytes such as NKT cells and CD8+ T cells; and/or, cause ICAM3 shedding from the surface of the ICAM3 expressing cell. Such agents may bind ICAM3 and trigger the induction and mobilization of novel immune cell populations into the blood. The ICAM3 modulating agent may be an ICAM3 antagonist/ICAM3 inhibitor, or may be an ICAM3 agonist/activator.

Such ICAM3 modulating agents may include, for example, anti-ICAM3 antibodies raised against ICAM3 or a portion thereof, small molecule modulators of ICAM3 (such as activators or inhibitors of ICAM3), and peptide agents/proteins which bind ICAM3. Suitable means of identifying ICAM3 modulating agents will be well known to those of skill in the art—for example, anti ICAM3 antibodies may be identified by a method which may include bringing into contact a library of antibody molecules and an ICAM3 epitope, and selecting one or more specific antibody molecules of the library able to bind said epitope. Alternatively, these could be identified using competition binding assays employing known anti ICAM3 antibodies, with competition determined, for example, using ELISA or flow cytometry. Similarly, small molecule modulators of ICAM3 may be identified by routine screening experiments such as radioligand binding assays and functional assays.

As already described above, the present application discloses the surprising capacity of glucocorticoid receptor modulating agents (such as dexamethasone and other glucocorticoids) to bind ICAM3 and exert modulating actions upon ICAM3. Thus, in some embodiments, the ICAM3 modulating agent may be a glucocorticoid-receptor (GR) modulating agent. As used herein, the term glucocorticoid-receptor (GR) modulating agent includes glucocorticoids, glucocorticoid receptor agonists, and any compound that binds to the glucocorticoid receptor. Glucocorticoid-receptor (GR) modulating agents such as glucocorticoids exert their effects through membrane bound GRs which induce rapid effects, and cytoplasmic GRs which activate or repress gene expression. Some of the desirable lymphodepletive effects of glucocorticoids and GR modulating agents are believed to be mediated via membrane GRs or other non-genomic effects in addition to their genomic effects. Glucocorticoids have been reported to have varied effects on lymphocyte levels, depending on the concentration of the glucocorticoid administered and the duration of treatment. In general, at low doses typically used for chronic therapy, glucocorticoids have been reported to redistribute lymphocytes from the peripheral blood into the bone marrow, at medium doses glucocorticoids have been reported to cause leukocytosis thought to be a redistribution of leukocytes from the bone marrow, spleen and thymus into the peripheral blood, and at higher doses glucocorticoids have a lymphotoxic action on lymphocytes by triggering apoptosis and necroptosis. The duration of effect also depends on the dose level; for instance Fauci et al (1976) reports a single oral 0.24 mg/kg dexamethasone dose suppresses peripheral blood T and B lymphocytes 80% with recovery beginning at 12 hours and normal levels by 24 hours. The present authors have previously demonstrated (in international patent application PCT/US2019/054395) that acute oral doses of 3 mg/kg or greater dexamethasone are necessary to reduce peripheral blood T and B cells 24-48 hours after administration, with return to baseline levels occurring around 5 to 28 days after dosing.

Glucocorticoid-receptor (GR) modulating agents which may be used in the disclosed methods include, for example, selective glucocorticoid receptor modulators (SEGRMs) and selective glucocorticoid receptor agonists (SEGRAs). Glucocorticoids, selective glucocorticoid receptor modulators, and selective glucocorticoid receptor agonists (SEGRAs) that may be utilized in the disclosed methods are well known to those skilled in the art.

Some such glucocorticoids include, but are not limited to, dexamethasone, dexamethasone containing agents, hydrocortisone, methylpredisone, prednisone, corticone, budesonide, betamethasone, ciclesonide, and beclomethasone. Other glucocorticoids include prednisolone, mometasone furoate, Triamcinolone Acetonide, and methylprednisolone.

Accordingly, in some preferred embodiments of the methods of the disclosure, the glucocorticoid-receptor (GR) modulating agent may be a glucocorticoid. In some such embodiments, the glucocorticoid may be selected from the group consisting of: dexamethasone, hydrocortisone, methylprednisolone, prednisone, prednisolone, prednylidene, cortisone, budesonide, betamethasone, flumethasone, ciclesonide, and beclomethasone. In some preferred embodiments, the glucocorticoid may be selected from the group consisting of: dexamethasone, betamethasone, and methylprednisone. In some particularly preferred embodiments the glucocorticoid may be dexamethasone or betamethasone.

In some embodiments of the methods of the disclosure, the glucocorticoid may be selected from the group consisting of: dexamethasone base, dexamethasone sodium phosphate, dexamethasone hemisuccinate, dexamethasone sodium succinate, dexamethasone succinate, dexamethasone isonicotinate, dexamethasone-21-acetate, dexamethasone phosphate, dexamethasone-21-phosphate, dexamethasone tebutate, dexamethasone valerate, dexamethasone acetate monohydrate, dexamethasone pivalate, dexamethasone palmitate, dexamethasone-21-palmitate, dexamethasone dipropionate, dexamethasone propionate, dexamethasone acetate anhydrous, dexamethasone-21-phenylpropionate, dexamethasone-21-sulfobenzoate, dexamethasone hemo-sulfate, dexamethasone sulfate, dexamethasone beloxil, dexamethasone acid, dexamethasone acefurate, dexamethasone carboximide, dexamethasone cipecilate, dexamethasone 21-phosphate disodium salt, dexamethasone mesylate, dexamethasone linoleate, dexamethasone glucoside, dexamethasone glucuronide, dexamethasone iodoacetate, dexamethasone oxetanone, carboxymethylthio-dexamethasone, dexamethasonebisethoximes, dexamethasone epoxide, dexamethasonelinolelaidate, dexamethasone methylorthovalerate, dexamethasone spermine, 6-hydroxy dexamethasone, dexamethasone tributylacetate, dexamethasone aspartic acid, dexamethasone galactopyranose, dexamethasone hydrochloride, hydroxy dexamethasone, carboxy dexamethasone, desoxy dexamethasone, dexamethasone butazone, dexamethasone cyclodextrin, dihydro dexamethasone, oxo dexamethasone, propionyloxy dexamethasone, dexamethasone galactodie, dexamethasone isonicotinate, dexamethasone sodium hydrogen phosphate, dexamethasone aldehyde, dexamethasone pivlate, dexamethasone tridecylate, dexamethasone crotonate, dexamethasone methanesulfonate, dexamethasone butylacetate, dehydro dexamethasone, dexamethasone Isothiocyanatoethyl)Thioether, dexamethasone bromoacetate, dexamethasone hemiglutarate, deoxy dexamethasone, dexamethasone chlorambucilate, dexamethasone melphalanate, formyloxy dexamethasone, dexamethasone butyrate, dexamethasone laurate, dexamethasone acetate, and any combination treatment that contains a form of dexamethasone. In some preferred embodiments, the glucocorticoid may be dexamethasone base or dexamethasone sodium phosphate.

In some embodiments of the disclosure, the glucocorticoid receptor modulating agent may not be one or more of the above recited agents.

Mechanism

In the Examples, the authors have shown that glucocorticoid molecules can bind intercellular adhesion molecules such as ICAM3 which is highly expressed on lymphocytes, monocytes and neutrophils, as well as on cancer cell types such as melanoma and osteosarcoma. By binding ICAM3, high dose glucocorticoids are able to exert a concentration dependent, direct killing effect on these cell types.

Accordingly, in the methods of the disclosure, the ICAM3 modulating agents induce cell death of ICAM3 expressing cells by binding to ICAM3. In some embodiments, the ICAM3 modulating agents induce apoptosis of ICAM3 expressing cells by binding to ICAM3. In some embodiments, the ICAM3 modulating agent triggers or supports an effective immune response against the ICAM3 expressing cells. In some embodiments, the ICAM3 modulating agent causes ICAM3 shedding from the surface of a cell into the extracellular space. In some embodiments, the ICAM3 modulating agent causes ICAM3 expressing cells to be marked for attack by immune cells. In some embodiments the ICAM3 modulating agent triggers (activates) cell apoptotic pathways.

In some embodiments, ICAM3 is the amino acid disclosed at UniProt accession no: P32942 (entry version 198) or a fragment thereof. In some embodiments, ICAM3 comprises an amino acid sequence having at least 70%, 80%, 90%, 95%, 99% or 100% sequence identity with the full-length of the amino acid sequence disclosed at UniProt accession no P32942 (entry version 198).

Biological Action by Marking Cells for Immune Attack

Monocytes and macrophages are phagocytic white blood cells which act in both non-specific and specific defense mechanisms in vertebrates. Their role is to phagocytose (engulf and then digest) dead and dying cells, cellular debris and pathogens either as stationary or as mobile cells, and to stimulate lymphocytes and other immune cells to respond to the pathogen. The molecular mechanisms underlying recruitment of phagocytic white blood cells is believed to involve recognition of molecular 'flags' on the surface of dying cell, that are bound and allow the dying cell to be eaten and destroyed (Gregory & Pound, 2010, hereby incorporated by reference in its entirety). ICAM3 has been shown to act as such a molecular 'flag' following a change of function on dying cells (Moffat et el 1999, hereby incorporated by reference in its entirety).

Thus, without being bound by theory, the present authors believe that the concentration-dependent mechanism of cell apoptosis observed following in vitro administration of acute high dose glucocorticoids (see Examples 1 and 2) may be mediated by binding of glucocorticoids to ICAM3 causing the ICAM3 expressing cells to become marked for attack by macrophages and/or leukocytes such as NKT cells and CD8+ T cells. These may include the immune cells that the present authors have shown are induced/mobilised by high concentrations of glucocorticoids, as described more fully below.

ICAM3 shedding may also occur following glucocorticoid binding: Juan, 1999, (which is hereby incorporated by reference in its entirety) describes that, after 24 hours, dexamethasone from 0.1 nanomolar up to 1 micromolar induced shedding of up to 28-33% of ICAM3 from eosinophils. The shedding described in Juan was near maximal (28%) at 0.01 micromolar: adding two logs additional dexamethasone elicited only modest further increases in shedding to 28% (+5%), which would not have motivated experts in the field to investigate higher concentrations of dexamethasone to determine further effects on ICAM3 shedding. ICAM3 shedding following glucocorticoid binding may further stimulate an immune response against these cell types by acting as a chemoattractant signal promoting recruitment of macrophages/phagocytes to the site of cells from which ICAM3 has been shed (described, for example, in Torr et al 2012, hereby incorporated by reference in its entirety). Cells recruited to the site of cells from which ICAM3 has been shed may include the immune cells that the present authors have shown are induced/mobilised by high concentrations of glucocorticoids, as described more fully below. The present authors hypothesize that ICAM3 shedding following dexamethasone binding may contribute to mobilisation of these novel immune cells after supra-high concentrations of glucocorticoids.

Thus, in some embodiments of the methods of the disclosure, the ICAM3 modulating agent causes ICAM3 shedding from the surface of a cell into the extracellular space.

In some embodiments, at least about 10, 20, 30, 35, 40, 45 50, 55, 60, 65, 70, 75 80, 85, 90, 95, 96, 97, 98, 99, or 99% of the total ICAM3 expressed by a cell is shed into the extracellular space. In some embodiments, the ICAM3 elicits at least about a 10, 20, 30, 35, 40, 45, 50, 55, 60, 65, 70, 75 80, 85, 90, 95, 96, 97, 98, 99, or 99% reduction in surface expression of ICAM3 on a cell. In some preferred embodiments, at least about 30 or 40% of the total ICAM3 expressed by a cell is shed into the extracellular space. In some preferred embodiments, the ICAM3 elicits at least about a 35 or 40% reduction in surface expression of ICAM3 on a cell. Suitable methods for determining extent and changes in ICAM3 expression and shedding are well known to those of skill in the art, for example the methods described in Juan et al (which is hereby incorporated by reference in its entirety).

Biological Action Via Induction of Immune Cells

High doses of glucocorticoid exert powerful biological effects that will contribute to the treatment of lymphocyte-mediated diseases and cancers, as well as microbial diseases. AVM0703 at human-equivalent dose (HED doses) of 15 mg/kg and above mobilizes a very active Natural Killer T cell that expresses CD3 at very high levels (AVM_NKT cells), which are not otherwise found in the circulation without this high dose treatment. This cell type is discussed in greater detail below.

At HED of 15 mg/kg dexamethasone phosphate and higher, besides mobilizing the abovementioned AVM_NKT cells, novel CD3-very-high T cell (which may express both CD4 and CD8), and CD11b-very-high dendritic cells are also induced. CD4CD8 double positivity on CD3 T lymphocytes indicates a cytotoxic T cell. Surprisingly, these doses of glucocorticoid do not appear to activate GRs because they have no activity at equivalent concentrations in vitro on whole blood or splenocytes (see Example 3, below), and in vivo there have been no effects on colon, pancreas or bone, which would be expected if GRs were being activated. In vivo only lymphocytes, monocytes, some neutrophils and cancer cells have been ablated. Almost complete ablation is seen just 6 hours after dexamethasone dosing, demonstrating a rapid onset of action.

AVM_NKT cells are NKp46+ and Ly6G positive, indicating the potential to directly kill targets as well as to engulf them. The typical AVM_NKT summarized above are not CD1d restricted. CD11b very high dendritic cells are also activated by these doses of AVM0703. In vivo, glucocorticoids ablate lymphocytes other than NK and NKT cells, and monocytes, within 6 hours after oral dosing of naïve mice. In tumor models the novel NKT and T cell are not observed in the blood. However, within 48 hours of dosing NKp46+ cells and Ly6G+ cells, which are not macrophages as they are negative for F4/80, can be found in formations within the tumors, surrounding regions of remaining viable tumor. This indicates the functional potency of these cells. In the tumor setting, the AVM novel immune cells are not observed in the blood. They appear to preferentially home to the abnormal cells, in this case cancer cells, and circulating normal monocytes and neutrophils are not depleted as they are in the naïve setting.

Beyond the known properties of NKT cells and the advantages of NKT cell-targeted immunotherapy, the novel AVM_NKT cells offer an additional advantage as they may add direct target cell engulfment to the known killing properties of other NKT like invariant NKT (iNKT) cells. This function is attributed to the AVM_NKT's unique expression of Ly6G. Moreover, the AVM_NKT are induced by high dose glucocorticoids and are thus, in principle, available in large numbers, in contrast to the limited numbers of natural NKT (and iNKT cells) that are insufficient for autologous therapy in the elderly, the ill, or cancer patients.

Dosages

In some embodiments of the methods of the disclosure, the ICAM3 modulating agent may be administered at a dose sufficient to block the signalling cascades caused by ICAM3 activation. In some embodiments of the methods of the disclosure, the ICAM3 modulating agent may be administered at a dose sufficient to activate the signalling cascades caused by ICAM3 activation. In some embodiments, the ICAM3 modulating agent is administered at a dose sufficient to cause ICAM3 shedding from the surface of a cell into the extracellular space. In some embodiments, the ICAM3 modulating agent is administered at a dose sufficient to cause ICAM3 expressing cells to be marked for attack by immune cells.

In embodiments of the methods of the disclosure in which the ICAM3 modulating agent is a glucocorticoid-receptor (GR) modulating agent, the glucocorticoid-receptor (GR) modulating agent may be administered at a dose equivalent to about at least 6 mg/kg human equivalent dose (HED) of dexamethasone base.

Equivalent doses of another glucocorticoid or glucocorticoid receptor modulating agent can be readily and easily calculated using publicly available corticoid conversion algorithms, preferably http://www.medcalc.com. By way of example, 3 to 12 mg/kg dexamethasone phosphate converts to 19 to 75 mg/kg prednisone. Since prednisone's biologic half-life is about 20 hours, while dexamethasone's biologic half-life is about 36 to 54 hours prednisone would be dosed between 19 to 75 mg/kg every 24 hours for equivalent biologic dosing. More specifically, a 12 mg/kg dose of dexamethasone phosphate corresponds to a 75 mg/kg dose of prednisolone that would require repeat dosing of about two to about three doses every 24 hours. A 10 mg/kg dose of betamethasone is about 12 mg/kg dexamethasone phosphate and has a pharmacodynamic (biologic) half-life similar to dexamethasone.

Dexamethasone doses in the examples in the present application are given as human equivalent doses (HED) Methods for calculating the human equivalent dose (HED) are known in the art. For example the FDA's Centre for Drug Evaluation and Research (CDER) issued a highly-cited guidance document in 2005 (U.S Department of Health CDER, 2005), which sets out the established algorithm for converting animal doses to HED based on body surface area (the generally accepted method for extrapolating doses between species) at Table 1 on page 7 of that document. For reference, Table 1 is reproduced below. The skilled person understands that the animal dose in mg/kg, explained below, the HED is calculated easily using the standard conversion factors in the right hand columns of Table 1:

TABLE 1

Conversion of Animal Doses to Human Equivalent
Doses Based on Body Surface Area

| | To Convert Animal Dose in mg/kg to HED[a] in mg/kg, Either: | | |
| | To Convert Animal | | |
| Species | Dose in mg/kg to Dose in mg/m², Multiply by k$_m$ | Divide Animal Dose By | Multiply Animal Dose By |
|---|---|---|---|
| Human | 37 | — | — |
| Child (20 kg)[b] | 25 | — | — |
| Mouse | 3 | 12.3 | 0.08 |
| Hamster | 5 | 7.4 | 0.13 |
| Rat | 6 | 6.2 | 0.16 |
| Ferret | 7 | 5.3 | 0.19 |
| Guinea pig | 8 | 4.6 | 0.22 |
| Rabbit | 12 | 3.1 | 0.32 |
| Dog | 20 | 1.8 | 0.54 |
| Primates: | | | |
| Monkeys[c] | 12 | 3.1 | 0.32 |
| Marmoset | 6 | 6.2 | 0.16 |
| Squirrel monkey | 7 | 5.3 | 0.19 |
| Baboon | 20 | 1.8 | 0.54 |
| Micro-pig | 27 | 1.4 | 0.73 |
| Mini-pig | 35 | 1.1 | 0.95 |

[a]Assumes 60 kg human. For species not listed or for weights outside the standard ranges, HED can be calculated from the following formula: HED = animal dose in mg/kg × (animal weight in kg/human weight in kg)$^{0.33}$.
[b]This k$_m$ value is provided for reference only since healthy children will rarely be volunteers for phase 1 trials.
[c]For example, cynomolgus, rhesus, and stumptail.

In some embodiments, the glucocorticoid-receptor (GR) modulating agent is administered at a dose equivalent to about at least 12 mg/kg human equivalent dose (HED) of dexamethasone base. In other preferred embodiments, the glucocorticoid-receptor (GR) modulating agent is administered at a dose equivalent to about at least 15 mg/kg human equivalent dose (HED) of dexamethasone base. In other preferred embodiments, the glucocorticoid-receptor (GR) modulating agent is administered at a dose equivalent to about at least 24 mg/kg human equivalent dose (HED) of dexamethasone base. In some preferred embodiments, the glucocorticoid-receptor (GR) modulating agent is administered at a dose equivalent to about 12 mg/kg human equivalent dose (HED) of dexamethasone base, about 15 mg/kg human equivalent dose (HED) of dexamethasone base, or about 18 mg/kg human equivalent dose (HED) of dexamethasone base, or about 24 mg/kg human equivalent dose (HED) of dexamethasone base, or about 30 mg/kg human equivalent dose (HED) of dexamethasone base, or about 45 mg/kg human equivalent dose (HED) of dexamethasone base.

In some embodiments of the methods of the disclosure, the glucocorticoid-receptor (GR) modulating agent is administered at a dose equivalent to about at least 6-45 mg/kg human equivalent dose (HED) of dexamethasone base; about at least 15-24 mg/kg human equivalent dose (HED) of dexamethasone base; about at least 6-12 mg/kg human equivalent dose (HED) of dexamethasone base; or about at least 12-15 mg/kg human equivalent dose (HED) of dexamethasone base; or about at least 18-30 mg/kg human equivalent dose (HED) of dexamethasone base.

In the methods of the disclosure, the glucocorticoid-receptor (GR) modulating agent may be administered as a single acute dose, or as a total dose given over about a 24, 48, or 72 hour period. In some preferred embodiments, the glucocorticoid-receptor (GR) modulating agent is administered as a single acute dose. In other preferred embodiments, the glucocorticoid-receptor (GR) modulating agent is administered as a total dose given over about a 72 hour period.

In some embodiments of the methods of the disclosure, the methods may comprise a step of administering one or more further doses of a glucocorticoid-receptor (GR) modulating agent to the subject.

In this context, the one or more doses are administered further to a first or preceding dose of glucocorticoid-receptor (GR) modulating agent and may therefore be termed subsequent or second, third, fourth, etc. doses. Accordingly, in some embodiments, the one or more further doses may be administered about 24, 48, 72, 96, 120, 144, or 168 hours after a preceding dose (administration). In some embodiments, the one or more further doses may be administered every about 24, 48, 72, 96, 120, 144, or 168 hours after a preceding dose (administration). In some other embodiments, the one or more further doses may be administered once every week, once every two weeks, once every three weeks, or once every month after a preceding dose (administration). In some other embodiments, the one or more further doses may be administered twice every week after a preceding dose (administration).

In some embodiments, the one or more further doses may be administered between about 24 hours and 168 hours after a preceding dose (administration). In other embodiments, the one or more further doses may be administered between about 24 hours and 120 hours, between about 24 hours and 72 hours, or between about 24 hours and 48 hours after a preceding dose (administration). In some other embodiments, the one or more further doses may be administered between about 48 hours and 168 hours, between about 48 hours and 120 hours, or between about 48 hours and 72 hours after a preceding dose (administration). In some other embodiments, the one or more further doses may be administered between about 72 hours and 168 hours, or between about 72 hours and 120 hours after a preceding dose (administration).

In some embodiments, a subsequent dose is given 7 days after the initial dose. In some embodiments, a subsequent dose is given 14 days after the initial dose. In some embodiments, a subsequent dose is given 21 days after the initial dose.

In some embodiments in which the subject has, is suspected of having, or has been diagnosed with a T cell lymphoma, the one or more further doses may be administered every 21 days, or every 14 days or every 5-7 days for a period of time that can be determined by a physician.

In some embodiments in which the subject has, is suspected of having, or has been diagnosed with a B cell lymphoma, the one or more further doses may be administered every 21 days, or every 14 days or every 5-7 days for a period of time that can be determined by a physician.

Subjects

The terms "subject" and "patient" are used interchangeably herein, and refer to a human or animal. In some embodiments of the methods of the disclosure, the subject may be mammalian. In some preferred embodiments, the subject may be human of any sex or race. In some embodiments, the human is an adult human. In some embodiments of the methods of the disclosure, the subject may be a healthy subject, such as a healthy adult human subject. In this context a healthy subject is a subject which is not afflicted with disease.

In some embodiments of the methods of the disclosure, the subject may have, be suspected of having, or have been diagnosed with a lymphocyte mediated disease or cancer.

In some embodiments of the disclosure, the subject may be a subject selected for treatment based on detecting or determining activity or expression of ICAM3 in a sample derived from the subject. In some such embodiments the subject is selected using a method selecting as described in more detail below.

Subject Selection

The present disclosure includes methods of selecting subjects suitable for treatment in the methods of treatment of the disclosure. As used herein, subjects who are considered suitable for treatment are those subjects who are expected to benefit from, or respond to, the treatment. Such methods may comprise detecting or determining activity or expression of ICAM3 in a sample derived from the subject.

In some cases, detecting expression of ICAM3 may include determining the level of ICAM3 expression in the sample. The level of ICAM3 may be determined quantitatively or semi-quantitatively. A subject may be determined to be suitable for treatment, or selected for treatment, if ICAM3 is expressed in the sample. A subject may be determined to be suitable for treatment, or selected for treatment, if the level of ICAM3 is elevated or overexpressed in the sample. In some cases, the level of ICAM3 may be determined relative to a control. The control may be any suitable control as could be readily selected by the skilled person. For example, the control may be a control sample of the same type of tissue as the sample, but from a subject who is known to be suitable for treatment with the methods of the disclosure, or from a subject who is known to not be suitable for treatment with the methods of the disclosure. The control sample may also be derived from cell lines known to express ICAM3 at a certain level.

The sample may be any suitable sample, and which may be taken from any tissue or bodily fluid, as could be readily selected by the skilled person. For example, the sample may comprise or may be derived from: a quantity of blood; a quantity of serum derived from the subject's blood; a tissue sample or biopsy; or cells isolated from said individual. In some cases the sample may be taken from a bodily fluid, more preferably one that circulates through the body. For example, the sample may be a blood sample or lymph sample. In some cases, the sample is a urine sample or a saliva sample. In some preferred embodiments, the sample may be a blood sample or blood-derived sample. The blood derived sample may be a selected fraction of a subject's blood, e.g. a selected cell-containing fraction or a plasma or serum fraction. A selected cell-containing fraction may contain cell types of interest such as lymphocytes. Accordingly, methods according to the present disclosure may involve detection of an ICAM3 polypeptide or nucleic acid in blood, in white blood cells, peripheral blood mononuclear cells, granulocytes, red blood cells and/or lymphocytes. Some preferred embodiments of the methods of the disclosure That is, in some preferred embodiments of the methods of the disclosure may involve detection of an ICAM3 polypeptide or nucleic acid in lymphocytes. That is, the sample may be a lymphocyte-containing sample. In other preferred embodiments the sample may be a tissue sample, such as a sample of tumor tissue, such as cancerous tumor tissue. The sample may have been obtained by a tumor biopsy.

In some embodiments, may be determined to be suitable for treatment, or selected for treatment, if 10%, 20%, 30%, 40%, 50% or more of the cells in the sample express ICAM3. For example, in cases in which the subject has an ICAM3-expressing cancer, a subject may be determined to be suitable for treatment if 10%, 20%, 30%, 40%, 50% or more of the tumor cells in a sample express ICAM3.

The level of ICAM3 expression may be determined by any suitable method known to the skilled person—for example, by immunohistochemistry or by another immunological technique Lymphocyte Mediated Disease ICAM3 is expressed at substantial levels on lymphocytes. The term "lymphocyte" as used herein includes natural killer (NK) cells, T cells, or B cells. NK cells are a type of cytotoxic (cell toxic) lymphocyte that represent a major component of the inherent immune system. NK cells reject tumors and cells infected by viruses. It works through the process of apoptosis or programmed cell death. They were termed "natural killers" because they do not require activation in order to kill cells. T-cells play a major role in cell-mediated-immunity (no antibody involvement). Its T-cell receptors (TCR) differentiate themselves from other lymphocyte types. The thymus, a specialized organ of the immune system, is primarily responsible for the T cell's maturation. There are six types of T-cells, namely: Helper T-cells (e.g., CD4+ cells), Cytotoxic T-cells (also known as TC, cytotoxic T lymphocyte, CTL, T-killer cell, cytolytic T cell, CD8+ T-cells or killer T cell), Memory T-cells ((i) stem memory T scM cells, like naive cells, are CD45RO−, CCR 7+, CD45RA+, CD62L+(L-selectin), CD27+, CD28+ and IL-7Ra+, but they also express large amounts of CD95, CXCR3, and LFA-1, and show numerous functional attributes distinctive of memory cells); (ii) central memory TcM cells express L-selectin and the CCR7, they secrete IL-2, but not IFNy or IL-4, and (iii) effector memory T EM cells, however, do not express L-selectin or CCR 7 but produce effector cytokines like IFNy and IL-4), Regulatory T-cells (Tregs, suppressor T cells, or CD4+CD25+ regulatory T cells), Natural Killer T-cells (NKT) and Gamma Delta T-cells. B-cells, on the other hand, play a principal role in humoral immunity (with antibody involvement). It makes antibodies and antigens and performs the role of antigen presenting cells (APCs) and turns into memory B-cells after activation by antigen interaction. In mammals, immature-cells are formed in the bone marrow, where its name is derived from.

Autoimmune disorders and other diseases that are mediated by immune cells including lymphocytes include, but are not limited by, the following list: allergies, asthma, residual HIV, germinal center lymphomas such as Burkitts Lymphoma and Diffuse Large B cell Lymphoma, marginal zone lymphoma, graft versus host disease (GvHD), steroid-resistant GvHD, acute lymphocytic leukemia or lymphoblastic leukemia (T-ALL or B-ALL), Achalasia, Addison's disease, Adult Still's disease, Agammaglobulinemia, Alopecia areata, Amyloidosis, Ankylosing spondylitis, Anti-GBM/Anti-TBM nephritis, Antiphospholipid syndrome, Autoimmune angioedema, Autoimmune dysautonomia, Autoimmune encephalomyelitis, Autoimmune hepatitis, Autoimmune inner ear disease (AIED), Autoimmune myocarditis, Autoimmune oophoritis, Autoimmune orchitis, Autoimmune pancreatitis, Autoimmune retinopathy, Autoimmune urticaria, Axonal & neuronal neuropathy (AMAN), Baló disease, Behcet's disease, Benign mucosal pemphigoid, Bullous pemphigoid, Castleman disease (CD), Celiac disease, Chagas disease, Chronic inflammatory demyelinating polyneuropathy (CIDP), Chronic recurrent multifocal osteomyelitis (CRMO), Churg-Strauss Syndrome (CSS) or Eosinophilic Granulomatosis (EGPA), Cicatricial pemphigoid, Cogan's syndrome, Cold agglutinin disease, Congenital heart block, Coxsackie myocarditis, CREST syndrome, Crohn's disease, Dermatitis herpetiformis, Dermatomyositis, Devic's disease (neuromyelitis optic), Discoid lupus, Dressler's syndrome, Endometriosis, Eosinophilic esophagitis (EoE), Eosinophilic fasciitis, Erythema *nodosum*, Essential mixed cryoglobulinemia, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis, Graves' disease, Guillain-Barre syndrome, Hashimoto's thyroiditis, Hemolytic anemia, Henoch-Schonlein purpura (HSP), Herpes gestationis or pemphigoid gestationis (PG), Hidradenitis Suppurativa (HS) (Acne Inversa), Hypogammalglobulinemia, IgA Nephropathy, IgG4-related sclerosing disease, Immune thrombocytopenic purpura (ITP), Inclusion body myositis (IBM), Interstitial cystitis (IC), Juvenile arthritis, Juvenile diabetes (Type 1 diabetes), Juvenile myositis (JM), Kawasaki disease, Lambert-Eaton syndrome, Leukocytoclastic vasculitis, Lichen planus, Lichen sclerosus, Ligneous conjunctivitis, Linear IgA disease (LAD), Lupus, Lyme disease chronic, Meniere's disease, Microscopic polyangiitis (MPA), Mixed connective tissue disease (MCTD), Mooren's ulcer, Mucha-Habermann disease, Multifocal Motor Neuropathy (MMN) or MMNCB, Multiple sclerosis, Myasthenia gravis, Myositis, Narcolepsy, Neonatal Lupus, Neuromyelitis optica, Neutropenia, Ocular cicatricial pemphigoid, Optic neuritis, Palindromic rheumatism (PR), PANDAS, Paraneoplastic cerebellar degeneration (PCD), Paroxysmal nocturnal hemoglobinuria (PNH), Parry Romberg syndrome, Pars planitis (peripheral uveitis), Parsonage-Turner syndrome, Pemphigus, Peripheral neuropathy, Perivenous encephalomyelitis, Pernicious anemia (PA), POEMS syndrome, Polyarteritis nodosa, Polyglandular syndromes type I, II, III, Polymyalgia rheumatica, Polymyositis, Postmyocardial infarction syndrome, Postpericardiotomy syndrome, Primary biliary cirrhosis, Primary sclerosing cholangitis, Progesterone dermatitis, Psoriasis, Psoriatic arthritis, Pure red cell aplasia (PRCA), Pyoderma gangrenosum, Raynaud's phenomenon, Reactive Arthritis, Reflex sympathetic dystrophy, Relapsing polychondritis, Restless legs syndrome (RLS), Retroperitoneal fibrosis, Rheumatic fever, Rheumatoid arthritis, Sarcoidosis, SARS CoV2 (COVID-19), Schmidt syndrome, Scleritis, Scleroderma, Sjögren's syndrome, Sperm & testicular autoimmunity, Stiff person syndrome (SPS), Subacute bacterial endocarditis (SBE), Susac's syndrome, Sympathetic ophthalmia (SO), Takayasu's arteritis, Temporal arteritis/Giant cell arteritis, Thrombocytopenic purpura (TTP), Tolosa-Hunt syndrome (THS), Transverse myelitis, Type 1 diabetes, Ulcerative colitis (UC), Undifferentiated connective tissue disease (UCTD), Uveitis, Vasculitis, Vitiligo, Vogt-Koyanagi-Harada Disease In some preferred embodiments, the lymphocyte mediated disease may be a cancer, such as a lymphoma, e.g. a germinal centre lymphoma (GC lymphoma) or marginal zone lymphoma.

In some embodiments, the lymphocyte mediated disease may be an autoimmune disease, or an immune mediated disease. "Autoimmune disease" as used herein refers to autoimmune disorders and other diseases arising from an abnormal immune in which the immune system aberrantly attacks a subject's own constituents. (In healthy subjects, the immune system avoids damaging autoimmune reactions by establishing tolerance to the subject's own constituents). Examples of various autoimmune diseases are described herein and include but are not limited to, celiac disease, diabetes mellitus type 1, Graves' disease, inflammatory bowel disease, transient osteoporosis, multiple sclerosis, psoriasis, rheumatoid arthritis, and systemic lupus erythematosus.

In some embodiments of the disclosure the immune mediated disease may be: allergies, asthma, graft versus host disease (GvHD), steroid-resistant GvHD, Achalasia, Addison's disease, Adult Still's disease, Agammaglobulinemia, Alopecia areata, Alopecia, transient osteoporosis, Amyloidosis, Ankylosing spondylitis, Anti-GBM/Anti-TBM nephritis, Antiphospholipid syndrome, Autoimmune angioedema, Autoimmune dysautonomia, Autoimmune encephalomyelitis, Autoimmune hepatitis, Autoimmune inner ear disease (AIED), Autoimmune myocarditis, Autoimmune oophoritis, Autoimmune orchitis, Autoimmune pancreatitis, Autoimmune retinopathy, Autoimmune urticaria, Axonal & neuronal neuropathy (AMAN), Baló disease, Behcet's disease, Benign mucosal pemphigoid, Bullous pemphigoid, Castleman disease (CD), Celiac disease, Chagas disease, Chronic inflammatory demyelinating polyneuropathy (CIDP), Chronic recurrent multifocal osteomyelitis (CRMO), Churg-Strauss Syndrome (CSS) or Eosinophilic Granulomatosis (EGPA), Cicatricial pemphigoid, Cogan's syndrome, Cold agglutinin disease, Congenital heart block, Coxsackie myocarditis, CREST syndrome, Crohn's disease, Dermatitis herpetiformis, Dermatomyositis, Devic's disease (neuromyelitis optic), Discoid lupus, Dressler's syndrome, Endometriosis, Eosinophilic esophagitis (EoE), Eosinophilic fasciitis, Erythema *nodosum*, Essential mixed cryoglobulinemia, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis, Graves' disease, Guillain-Barre syndrome, Hashimoto's thyroiditis, Hemolytic anemia, Henoch-Schonlein purpura (HSP), Herpes gestationis or pemphigoid gestationis (PG), Hidradenitis Suppurativa (HS) (Acne Inversa), Hypogammalglobulinemia, IgA Nephropathy, IgG4-related sclerosing disease, Immune thrombocytopenic purpura (ITP), Inclusion body myositis (IBM), Interstitial cystitis (IC), Juvenile arthritis, Juvenile diabetes (Type 1 diabetes), Juvenile myositis (JM), Kawasaki disease, Lambert-Eaton syndrome, Leukocytoclastic vasculitis, Lichen planus, Lichen sclerosus, Ligneous conjunctivitis, Linear IgA disease (LAD), Lupus, Lyme disease chronic, Meniere's disease, Microscopic polyangiitis (MPA), Mixed connective tissue disease (MCTD), Mooren's ulcer, Mucha-Habermann disease, Multifocal Motor Neuropathy (MMN) or MMNCB, Multiple sclerosis, Myasthenia gravis, Myositis, Narcolepsy, Neonatal Lupus, Neuromyelitis optica, Neutropenia, Ocular cicatricial pemphigoid, Optic neuritis, Palindromic rheumatism (PR), PANDAS, Paraneoplastic cerebellar degeneration (PCD), Paroxysmal nocturnal hemoglobinuria (PNH), Parry Romberg syndrome, Pars planitis (peripheral uveitis), Parsonage-Turner syndrome, Pemphigus, Peripheral neuropathy, Perivenous encephalomyelitis, Pernicious anemia (PA), POEMS syndrome, Polyarteritis nodosa, Polyglandular syndromes type I, II, III, Polymyalgia rheumatica, Polymyositis, Postmyocardial infarction syndrome, Postpericardiotomy syndrome, Primary biliary cirrhosis, Primary sclerosing cholangitis, Progesterone dermatitis, Psoriasis, Psoriatic arthritis, Pure red cell aplasia (PRCA), Pyoderma gangrenosum, Raynaud's phenomenon, Reactive Arthritis, Reflex sympathetic dystrophy, Relapsing polychondritis, Restless legs syndrome (RLS), Retroperitoneal fibrosis, Rheumatic fever, Rheumatoid arthritis, Sarcoidosis, Schmidt syndrome, Scleritis, Scleroderma, Sjögren's syndrome, Sperm & testicular autoimmunity, Stiff person syndrome (SPS), Subacute bacterial endocarditis (SBE), Susac's syndrome, Sympathetic ophthalmia (SO), Takayasu's arteritis, Temporal arteritis/Giant cell arteritis, Thrombocytopenic purpura (TTP), Tolosa-Hunt syndrome (THS), Transverse myelitis, Type 1 diabetes, Ulcerative colitis (UC), Undifferentiated connective tissue disease (UCTD), Uveitis, Vasculitis, Vitiligo, Vogt-Koyanagi-Harada Disease, Hemophagocytic lymphohistiocytosis, multiple myeloma, allergen specific immunotherapy, autosomal dominant haploinsufficiency, anterior interosseous nerve syndrome, Churg-Strauss syndrome, Systemic vasculitis, chronic graft versus host disease, Opsoclonus-Myoclonus Syndrome, Necrotising Autoimmune Myopathy (NAM), Pulmonary Sarcomatoid carcinomas, Waldenstrom's macroglobulinaemia (WM), fertility, Behcets Disease, Alopecia areata (AA), Acute-on-chronic Liver Failure, melanoma, 'organizing bronchiolitis syndrome', or encephalitis. In some embodiments the autoimmune disease may be: rheumatoid arthritis, rheumatic fever, multiple Sclerosis, experimental autoimmune encephalomyelitis, psoriasis, uveitis, diabetes mellitus, Systemic lupus erythematosus (SLE), lupus nephritis, eczema, Scleroderma, polymyositis/scleroderma, polymyositis/dermatomyositis, uncerative protitis, severe combined immunodeficiency (SCID), DiGeorge syndrome, ataxia-telangiectasia, seasonal allergies, perennial allergies, food allergies, anaphylaxis, mastocytosis, allergic rhinitis, atopic dermatitis, Parkinson's, Alzheimer's, hypersplenism, leukocyte adhesion deficiency, X-linked lymphoproliferative disease, X-linked agammaglobulinemia, selective immuno globulin A deficiency, hyper IgM syndrome, HIV, autoimmune lymphoproliferative syndrome, Wiskott-Aldrich syndrome, chronic granulomatous disease, common variable immunodeficiency (CVID), hyperimmunoglobulin E syndrome, Hashimoto's thyroiditis, acute idiopathic thrombocytopenic purpura, chronic idiopathic thrombocytopenia pur pura, dermatomyositis, Sydenham's chorea, myasthenia gravis, polyglandular syndromes, bullous pemphigoid, Henoch-Schonlein purpura, poststreptococcalnephritis, erythema nodosum, erythema multiforme, gA nephropathy, Takayasu's arteritis, Addison's disease, sarcoidosis, ulcerative colitis, polyarteritis nodosa, ankylosing spondylitis, Goodpasture's syndrome, thromboangitisubiterans, Sjogren's syndrome, primary biliary cirrhosis, Hashimoto's thyroiditis, thyrotoxicosis, chronic active hepatitis, polychondritis, pamphigus Vulgaris, Wegener's granulomatosis, membranous nephropathy, amyotrophic lateral Sclerosis, tabesdorsalis, giant cell arteritis/polymyalgia, peraiciousa nemia, rapidly progressive glomerulonephritis, psoriasis, fibrosing alveolitis, or cancer.

In some embodiments of the disclosure, the immune mediated disease may not be one of the above recited immune diseases.

In some preferred embodiments of the disclosure, the autoimmune disease may be selected from the group consisting of: multiple sclerosis, systemic sclerosis, amyotrophic lateral sclerosis, type 1 diabetes mellitus (T1D), scleroderma, pemphigus, and lupus. In some other preferred embodiments of the disclosure the autoimmune disease may be selected from the group consisting of: graft versus host disease (GvHD), and an allergic disorder such as asthma. In some embodiments of the disclosure lymphocyte mediated disease may be residual HIV disease.

Cancer

As used herein, "cancer" refers to a disease characterized by the uncontrolled growth of aberrant cells. Cancer cells can spread locally or through the bloodstream and lymphatic system to other parts of the body. Examples of various cancers are described herein and include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like. The terms "tumor" and "cancer" are used interchangeably herein, e.g., both terms encompass solid and liquid, e.g., diffuse or circulating, tumors. As used herein, the term "cancer" or "tumor" includes premalignant, as well as malignant cancers and tumors.

In the methods of the disclosure the cancer is an ICAM3-expressing cancer, such as an ICAM3-expressing lymphoma. In some embodiments of the disclosure, the cancer may be: Malignant neoplasm of lip, Malignant neoplasm of tonsil, Malignant neoplasm of tongue, Malignant neoplasm of gum, Malignant neoplasm of mouth, Malignant neoplasm of parotid gland, Malignant neoplasm of salivary glands, Malignant neoplasm of pharynx, Malignant neoplasm of esophagus, Malignant neoplasm of stomach, Malignant neoplasm of small intestine, Malignant neoplasm of colon, Malignant neoplasm of recto sigmoid junction, Malignant neoplasm of rectum, Malignant neoplasm of anus, Malignant neoplasm of liver, Malignant neoplasm of gallbladder, Malignant neoplasm of biliary tract, Malignant neoplasm of pancreas, Malignant neoplasm of intestinal tract, Malignant neoplasm of spleen, Malignant neoplasm of nasal cavity and middle ear, Malignant neoplasm of accessory sinuses, Malignant neoplasm of larynx, Malignant neoplasm of trachea, Malignant neoplasm of bronchus and lung, Malignant neoplasm of thymus, Malignant neoplasm of heart, mediastinum and pleura, Malignant neoplasm of sites in the respiratory system and intrathoracic organs, Malignant neoplasm of bone and articular cartilage of limbs, Malignant neoplasm of bones of skull and face, Malignant neoplasm of vertebral column, Malignant neoplasm of ribs, sternum and clavicle, Malignant neoplasm of pelvic bones, sacrum and coccyx, Malignant melanoma of skin, Malignant melanoma of lip, Malignant melanoma of eyelid, including canthus, Malignant melanoma of ear and external auricular canal, Malignant melanoma of face, Malignant melanoma of anal skin, Malignant melanoma of skin of breast, Malignant melanoma of limbs, including shoulder, Merkel cell carcinoma, Basal cell carcinoma of skin of lip, Squamous cell carcinoma of skin of lip, Other and unspecified malignant neoplasm skin/eyelid, including canthus, Malignant neoplasm skin/ear and external auric canal, Other and unspecified malignant neoplasm skin/and unspecified parts of face, Basal cell carcinoma of skin of other and unspecified parts of face, Squamous cell carcinoma of skin of and unspecified parts of face, Basal cell carcinoma of skin of scalp and neck, Squamous cell carcinoma of skin of scalp and neck, Basal cell carcinoma of skin of trunk, Basal cell carcinoma of anal skin, Basal cell carcinoma of skin of breast, Squamous cell carcinoma of skin of trunk, Squamous cell carcinoma of anal skin, Squamous cell carcinoma of skin of breast, Squamous cell carcinoma of skin of other part of trunk, Other and unspecified malignant neoplasm skin/limbs including shoulder, Basal cell carcinoma skin/limbs, including shoulder, Squamous cell carcinoma skin/limbs, including shoulder, Basal cell carcinoma of skin of limbs, including hip, Squamous cell carcinoma of skin of limbs, including hip, Mesothelioma, Kaposi's sarcoma, Malignant neoplasm of peripheral nerves and autonomic nervous sys, Malignant neoplasm of retroperitoneum and peritoneum, Malignant neoplasm of other connective and soft tissue, Malignant neoplasm of connective and soft tissue of thorax, Malignant neoplasm of connective and soft tissue of abdomen, Malignant neoplasm of connective and soft tissue of pelvis, Malignant neoplasm of conn and soft tissue of trunk, unspecified, Malignant neoplasm of overlapping sites of connective and soft tissue, Malignant neoplasm of connective and soft tissue, unspecified, Gastrointestinal stromal tumor, Malignant neoplasm of breast, Malignant neoplasm of vulva, Malignant neoplasm of vagina, Malignant neoplasm of cervix uteri, Malignant neoplasm of corpus uteri, Malignant neoplasm of uterus, part unspecified, Malignant neoplasm of ovary, Malignant neoplasm of other and unspecified female genital organs, Malignant neoplasm of placenta, Malignant neoplasm of penis, Malignant neoplasm of prostate, Malignant neoplasm of testis, Malignant neoplasm of other and unspecified male genital organs, Malignant neoplasm of kidney, Malignant neoplasm of renal pelvis, Malignant neoplasm of ureter, Malignant neoplasm of bladder, Malignant neoplasm of other and unspecified urinary organs, Malignant neoplasm of eye and adnexa, Malignant neoplasm of meninges, Malignant neoplasm of brain, Malignant neoplasm of spinal cord, cranial nerves, Malignant neoplasm of optic nerve, Malignant neoplasm of other and unspecified cranial nerves, Malignant neoplasm of central nervous system, unspecified, Malignant neoplasm of thyroid gland, Malignant neoplasm of adrenal gland, Malignant neoplasm of endo glands and related structures, Malignant neuroendocrine tumors, Malignant carcinoid tumors, Secondary neuroendocrine tumors, Malignant neoplasm of head, face and neck, Malignant neoplasm of thorax, Malignant neoplasm of abdomen, Malignant neoplasm of pelvis, Malignant neoplasm of limbs, Malignant neoplasm of lower limb, Secondary and unspecified malignant neoplasm of lymph nodes, Secondary malignant neoplasm of respiratory and digestive organs, Secondary malignant neoplasm of kidney and renal pelvis, Secondary malignant neoplasm of bladder and other and unspecified urinary organs, Secondary malignant neoplasm of skin, Secondary malignant neoplasm of brain and cerebral meninges, Secondary malignant neoplasm of and unspecified parts of nervous sys, Secondary malignant neoplasm of bone and bone marrow, Secondary malignant neoplasm of ovary, Secondary malignant neoplasm of adrenal gland, Hodgkin lymphoma, Follicular lymphoma, Non-follicular lymphoma, Small cell B-cell lymphoma, Mantle cell lymphoma, Diffuse large B-cell lymphoma, Lymphoblastic (diffuse) lymphoma, Burkitt lymphoma, Other non-follicular lymphoma, Non-follicular (diffuse) lymphoma, unspecified, Mature T/NK-cell lymphomas, Sezary disease, Peripheral T-cell lymphoma, not classified, Anaplastic large cell lymphoma, ALK-positive, Anaplastic large cell lymphoma, ALK-negative, Cutaneous T-cell lymphoma, unspecified, Other mature T/NK-cell lymphomas, Mature T/NK-cell lymphomas, unspecified, Other and unspecified types of non-Hodgkin lymphoma, Malignant immunoproliferative dis and certain other B-cell lymph, Multiple myeloma and malignant plasma cell neoplasms, Lymphoid leukemia, Acute lymphoblastic leukemia [ALL], Chronic lymphocytic leukemia of B-cell type, Prolymphocytic leukemia of B-cell type, Hairy cell leukemia, Adult T-cell lymphoma/leukemia (HTLV-1-associated), Prolymphocytic leukemia of T-cell type, Mature B-cell leukemia Burkitt-type, Other lymphoid leukemia, Lymphoid leukemia, unspecified, Myeloid leukemia, Acute myeloblastic leukemia, Chronic myeloid leukemia, BCR/ABL-positive, Atypical chronic myeloid leukemia, BCR/ABL-negative, Myeloid sarcoma, Acute promyelocytic leukemia, Acute myelomonocytic leukemia, Acute myeloid leukemia with 11q23-abnormality, Other myeloid leukemia, Myeloid leukemia, unspecified, Monocytic leukemia, Chronic myelomonocytic leukemia, Juvenile myelomonocytic leukemia, Other monocytic leukemia, Monocytic leukemia, unspecified, Other leukemias of specified cell type, Acute erythroid leukemia, Acute megakaryoblastic leukemia, Mast cell leukemia, Acute panmyelosis with myelofibrosis, Myelodysplastic disease, not classified, Other specified leukemias, Leukemia of unspecified cell type, Chronic leukemia of unspecified cell type, Leukemia, unspecified, Other & unspecified malignant neoplasm of lymphoid, hematopoietic tissue, Carcinoma in situ of oral cavity, esophagus and stomach, Carcinoma in situ of colon, Carcinoma in situ of recto sigmoid junction, Carcinoma in situ of rectum, Carcinoma in situ of anus and anal canal, Carcinoma in situ of other and unspecified parts of intestine, Carcinoma in situ of unspecified part of intestine, Carcinoma in situ of other parts of intestine, Carcinoma in situ of liver, gallbladder and bile ducts, Carcinoma in situ of other specified digestive organs, Carcinoma in situ of digestive organ, unspecified, Carcinoma in situ of middle ear and respiratory system, Carcinoma in situ of larynx, Carcinoma in situ of trachea, Carcinoma in situ of bronchus and lung, Carcinoma in situ of other parts of respiratory system, Melanoma in situ, Melanoma in situ of lip, Melanoma in situ of eyelid, including canthus, Melanoma in situ of ear and external auricular canal, Melanoma in situ of unspecified part of face, Melanoma in situ of scalp and neck, Melanoma in situ of trunk, Melanoma in situ of anal skin, Melanoma in situ of breast (skin) (soft tissue), Melanoma in situ of upper limb, including shoulder, Melanoma in situ of lower limb, including hip, Melanoma in situ of other sites, Carcinoma in situ of skin, Carcinoma in situ of skin of lip, Carcinoma in situ of skin of eyelid, including canthus, Carcinoma in situ skin of ear and external auricular canal, Carcinoma in situ of skin of other and unspecified parts of face, Carcinoma in situ of skin of scalp and neck, Carcinoma in situ of skin of trunk, Carcinoma in situ of skin of upper limb, including shoulder, Carcinoma in situ of skin of lower limb, including hip, Carcinoma in situ of skin of other sites, Carcinoma in situ of breast, Lobular carcinoma in situ of breast, Intraductal carcinoma in situ of breast, Other specified type of carcinoma in situ of breast, Unspecified type of carcinoma in situ of breast, Carcinoma in situ of cervix uteri, Carcinoma in situ of other parts of cervix, Carcinoma in situ of cervix, unspecified, Carcinoma in situ of other and unspecified genital organs, Carcinoma in situ of endometrium, Carcinoma in situ of vulva, Carcinoma in situ of vagina, Carcinoma in situ of other and unspecified female genital organs, Carcinoma in situ of penis, Carcinoma in situ of prostate, Carcinoma in situ of unspecified male genital organs, Carcinoma in situ of scrotum, Carcinoma in situ of other male genital organs, Carcinoma in situ of bladder, Carcinoma in situ of other and unspecified urinary organs, Carcinoma in situ of eye, Carcinoma in situ of thyroid and other endocrine glands, Benign neoplasm of mouth and pharynx, Benign neoplasm of major salivary glands, Benign neoplasm of colon, rectum, anus and anal canal, Benign neoplasm of and ill-defined parts of digestive system, Benign neoplasm of esophagus, Benign neoplasm of stomach, Benign neoplasm of duodenum, Benign neoplasm of other and unspecified parts of small intestine, Benign neoplasm of liver, Benign neoplasm of extrahepatic bile ducts, Benign neoplasm of pancreas, Benign neoplasm of endocrine pancreas, Benign neoplasm of ill-defined sites within the digestive system, Benign neoplasm of middle ear and respiratory system, Benign neoplasm of respiratory system, unspecified, Benign neoplasm of other and unspecified intrathoracic organs, Benign neoplasm of thymus, Benign neoplasm of heart, Benign neoplasm of mediastinum, Benign neoplasm of other specified intrathoracic organs, Benign neoplasm of intrathoracic organ, unspecified, Benign neoplasm of bone and articular cartilage, Benign neoplasm of short bones of upper limb, Benign neoplasm of long bones of lower limb, Benign neoplasm of short bones of lower limb, Benign neoplasm of bones of skull and face, Benign neoplasm of lower jaw bone, Benign neoplasm of vertebral column, Benign neoplasm of ribs, sternum and clavicle, Benign neoplasm of pelvic bones, sacrum and coccyx, Benign neoplasm of bone and articular cartilage, unspecified, Benign lipomatous neoplasm, Ben lipomatous neoplasm of skin, subcutaneous of head, face and neck, Benign lipomatous neoplasm of intrathoracic organs, Benign lipomatous neoplasm of intra-abdominal organs, Benign lipomatous neoplasm of spermatic cord, Benign lipomatous neoplasm of other sites, Benign lipomatous neoplasm of kidney, Benign lipomatous neoplasm of other genitourinary organ, Hemangioma and lymphangioma, any site, Hemangioma, Hemangioma unspecified site, Hemangioma of skin and subcutaneous tissue, Hemangioma of intracranial structures, Hemangioma of intra-abdominal structures, Hemangioma of other sites, Lymphangioma, any site, Benign neoplasm of mesothelial tissue, Benign neoplasm of soft tissue of retroperitoneum and peritoneum, Other benign neoplasms of connective and other soft tissue, Melanocytic nevi, Melanocytic nevi of lip, Melanocytic nevi of eyelid, including canthus, Melanocytic nevi of unspecified eyelid, including canthus, Melanocytic nevi of ear and external auricular canal, Melanocytic nevi of other and unspecified parts of face, Melanocytic nevi of scalp and neck, Melanocytic nevi of trunk, Melanocytic nevi of upper limb, including shoulder, Melanocytic nevi of lower limb, including hip, Melanocytic nevi, unspecified, Other benign neoplasm of skin of eyelid, including canthus, Other benign neoplasm skin/ear and external auricular canal, Other benign neoplasm skin/left ear and external auric canal, Other benign neoplasm of skin of other and unspecified parts of face, Other benign neoplasm of skin of other parts of face, Other benign neoplasm of skin of scalp and neck, Other benign neoplasm of skin of trunk, Other benign neoplasm skin/upper limb, including shoulder, Other benign neoplasm of skin of lower limb, including hip, Other benign neoplasm of skin, unspecified, Benign neoplasm of breast, Benign neoplasm of unspecified breast, Leiomyoma of uterus, Other benign neoplasms of uterus, Benign neoplasm of ovary, Benign neoplasm of other and unspecified female genital organs, Benign neoplasm of male genital organs, Benign neoplasm of urinary organs, Benign neoplasm of kidney, Benign neoplasm of renal pelvis, Benign neoplasm of ureter, Benign neoplasm of bladder, Benign neoplasm of urethra, Benign neoplasm of other specified urinary organs, Benign neoplasm of urinary organ, unspecified, Benign neoplasm of eye and adnexa, Benign neoplasm of conjunctiva, Benign neoplasm of cornea, Benign neoplasm of retina, Benign neoplasm of choroid, Benign neoplasm of ciliary body, Benign neoplasm of lacrimal gland and duct, Benign neoplasm of unspecified site of orbit, Benign neoplasm of unspecified part of eye, Benign neoplasm of meninges, Benign neoplasm of brain and central nervous system, Benign neoplasm of thyroid gland, Benign neoplasm of other and unspecified endocrine glands, Benign neoplasm of other and unspecified sites, Benign neoplasm of lymph nodes, Benign neoplasm of peripheral nerves and autonomic nervous sys, Benign neoplasm of other specified sites, Benign neuroendocrine tumors, Other benign neuroendocrine tumors, Neoplasm of uncertain behavior of oral cavity and digestive organs, Neoplasm of uncertain behavior of the major salivary glands, Neoplasm of uncertain behavior of pharynx, Neoplasm of uncertain behavior of sites of the oral cavity, Neoplasm of uncertain behavior of stomach, Neoplasm of uncertain behavior of small intestine, Neoplasm of uncertain behavior of appendix, Neoplasm of uncertain behavior of colon, Neoplasm of uncertain behavior of rectum, Neoplasm of uncertain behavior of liver, GB & bile duct, Neoplasm of uncertain behavior of other digestive organs, Neoplasm of uncertain behavior of digestive organ, Neoplasm of mid ear and intrathoracic organs, Neoplasm of uncertain behavior of larynx, Neoplasm of uncertain behavior of trachea, bronchus and lung, Neoplasm of uncertain behavior of pleura, Neoplasm of uncertain behavior of mediastinum, Neoplasm of uncertain behavior of thymus, Neoplasm of uncertain behavior of other respiratory organs, Neoplasm of uncertain behavior of respiratory organ, unspecified, Neoplasm of uncertain behavior of female genital organs, Neoplasm of uncertain behavior of uterus, Neoplasm of uncertain behavior of ovary, Neoplasm of uncertain behavior of unspecified ovary, Neoplasm of uncertain behavior of placenta, Neoplasm of uncertain behavior of male genital organs, Neoplasm of uncertain behavior of urinary organs, Neoplasm of uncertain behavior of kidney, Neoplasm of uncertain behavior of unspecified kidney, Neoplasm of uncertain behavior of renal pelvis, Neoplasm of uncertain behavior of ureter, Neoplasm of uncertain behavior of bladder, Neoplasm of uncertain behavior of other urinary organs, Neoplasm of uncertain behavior of unspecified urinary organ, Neoplasm of uncertain behavior of meninges, Neoplasm of uncertain behavior of cerebral meninges, Neoplasm of uncertain behavior of spinal meninges, Neoplasm of uncertain behavior of meninges, unspecified, Neoplasm of uncertain behavior of brain, Neoplasm of uncertain behavior of brain, infratentorial, Neoplasm of uncertain behavior of brain, unspecified, Neoplasm of uncertain behavior of cranial nerves, Neoplasm of uncertain behavior of spinal cord, Neoplasm of uncertain behavior of central nervous system, Neoplasm of uncertain behavior of endocrine glands, Neoplasm of uncertain behavior of thyroid gland, Neoplasm of uncertain behavior of adrenal gland, Neoplasm of uncertain behavior of unspecified adrenal gland, Neoplasm of uncertain behavior of parathyroid gland, Neoplasm of uncertain behavior of pituitary gland, Neoplasm of uncertain behavior of craniopharyngeal duct, Neoplasm of uncertain behavior of pineal gland, Neoplasm of uncertain behavior of carotid body, Neoplasm of uncertain behavior of aortic body and other paraganglia, Neoplasm of uncertain behavior of unspecified endocrine gland, Polycythemia vera, Myelodysplastic syndromes, Refractory anemia without ring sideroblasts, so stated, Refractory anemia with ring sideroblasts, Refractory anemia with excess of blasts [RAEB], Myelodysplastic syndrome, unspecified, Other neoplasm of uncertain behavior of lymphoid, hematopoietic tissue, Histiocytic and mast cell tumors of uncertain behavior, Chronic myeloproliferative disease, Monoclonal gammopathy, Essential (hemorrhagic) thrombocythemia, Osteomyelofibrosis, Other neoplasm of uncertain behavior of lymphoid, hematopoietic tissue, Neoplasm of uncertain behavior of lymphoid, hematopoietic & unspecified, Neoplasm of uncertain behavior of other and unspecified sites, Neoplasm of uncertain behavior of bone/artic cartilage, Neoplasm of uncertain behavior of connective/soft tissue, Neoplasm of uncertain behavior of peripheral nerves and autonomous nervous sys, Neoplasm of uncertain behavior of retroperitoneum, Neoplasm of uncertain behavior of peritoneum, Neoplasm of uncertain behavior of skin, Neoplasm of uncertain behavior of breast, Neoplasm of unspecified behavior of digestive system, Neoplasm of unspecified behavior of respiratory system, Neoplasm of unspecified behavior of bone, soft tissue, and skin, Neoplasm of unspecified behavior of breast, Neoplasm of unspecified behavior of bladder, Neoplasm of unspecified behavior of other genitourinary organs, Neoplasm of unspecified behavior of kidney, Neoplasm of unspecified behavior of other GU organ, Neoplasm of unspecified behavior of brain, Neoplasm of unspecified behavior of endo glands and other parts of nervous sys, Neoplasm of unspecified behavior of retina and choroid, or Neoplasm of unspecified behavior of unspecified site.

In some embodiments of the disclosure, the cancer may not be one of the above recited cancers.

In some embodiments of the disclosure, the cancer may be selected from the group consisting of: lymphoma, squamous cell cancer (such as epithelial squamous cell cancer); lung cancer, including small-cell lung cancer, non-small cell lung cancer, adenocarcinoma of the lung and squamous carcinoma of the lung; cancer of the peritoneum; hepatocellular cancer; gastric or stomach cancer, including gastrointestinal cancer; pancreatic cancer; glioblastoma; cervical cancer; ovarian cancer; liver cancer; bladder cancer; hepatoma; breast cancer; colon cancer; rectal cancer; colorectal cancer; endometrial or uterine carcinoma; salivary gland carcinoma; kidney or renal cancer; prostate cancer; vulval cancer; thyroid cancer; hepatic carcinoma; anal carcinoma; penile carcinoma; and head and neck cancer.

In some preferred embodiments of the disclosure the cancer may be selected from the group consisting of: lymphoma, osteosarcoma, and melanoma.

In some particularly preferred embodiments of the disclosure the cancer may be lymphoma. In more particularly preferred embodiments of the disclosure the cancer may be a B cell lymphoma or a T cell lymphoma. In some particularly preferred embodiments of the disclosure the cancer may be non-Hodgkin lymphoma.

In this context, "treat" means to exert a beneficial therapeutic effect in the subject, which can be any overall clinical benefit derived from the methods of the disclosure. This overall clinical benefit can be any of, for example: prolonged survival, partial or complete disease remission, (for example, as assessed by % bone marrow myeloblasts and/or normal maturation of cell lines), slowing or absence of disease progression (for example, as assessed by change in % bone marrow myeloblasts), tumour shrinkage (for example, a reduction in tumour volume of 5, 10, 20, 30, 40% or more), reduction in tumour burden (for example, a reduction in tumour burden of 5, 10, 20, 30, 40% or more), slowing or absence of tumour enlargement, slowing or absence of increase in tumour burden, improved quality of life (for example, as assessed using a health-related quality of life questionnaire such as a Functional Assessment of Cancer Therapy (FACT) questionnaire), progression-free survival, overall survival, hematologic improvement (for example: increased blood haemoglobin, platelet count, and/or neutrophil count), bone marrow response (for example: bone marrow with ≤5% myeloblasts; 30%, 40%, 50% or more reduction in bone marrow myeloblasts; absence of circulating myeloblasts and myeloblasts with Auer rods; absence of extramedullary disease), hematologic recovery (for example: ≥11 g/dL haemoglobin, ≥100×109/L platelets, and/or ≥1×109/L neutrophils in peripheral blood), negative response for a genetic marker (for example, CEBPA, NPM1, or FLT3), or any other positive patient outcome.

The overall clinical benefit may be an "anti-tumor effect". As used herein, an "anti-tumor effect" refers to a biological effect that can present as a decrease in tumor volume, a decrease in the number of tumor cells, a decrease in tumor cell proliferation, a decrease in the number of metastases, an increase in overall or progression-free survival, an increase in life expectancy, or amelioration of various physiological symptoms associated with the tumor. An anti-tumor effect can also refer to the prevention of the occurrence of a tumor, e.g., a vaccine. Suitable methods for determining tumour volume/burden are well known to the skilled person, for example, using: computed tomography (CT), or magnetic resonance imaging (MM) imaging technologies; X-ray imaging, for example, mammography; ultrasound imaging; nuclear imaging, for example positron emission tomography (PET), PET/CT scans, bone scans, gallium scans, or metaiodobenzylguanidine (MIBG) scans; bioluminescence imaging (BLI); fluorescence imaging (FLI); BD ToF (infra-red-based 3D Time-of-Flight camera) imaging.

Microbial Disease

As used herein, "microbial disease" (also termed "infectious disease") refers to a disease or illness resulting from the infection of a subject's body by infectious agents (pathogens) such as viruses, bacteria, or fungi. In some embodiments of the disclosure the infectious disease may be: *Acinetobacter* infections (*Acinetobacter baumannii*), Actinomycosis (*Actinomyces israelii, Actinomyces gerencseriae* and *Propionibacterium propionicus*) African sleeping sickness or African trypanosomiasis (*Trypanosoma brucei*), AIDS (Acquired immunodeficiency syndrome) (Human immunodeficiency virus), Amebiasis (*Entamoeba histolytica*), Anaplasmosis (*Anaplasma* species), Angiostrongyliasis (*Angiostrongylus*), Anisakiasis (*Anisakis*), Anthrax (*Bacillus anthracia*), Arcanobacterium haemolyticum infection (*Arcanobacterium haemolyticum*), Argentine hemorrhagic fever (Junin virus), Ascariasis (*Ascaris lumbricoides*), Aspergillosis (*Aspergillus* species), Astrovirus infection (Astroviridae family), Babesiosis (*Babesia* species), *Bacillus cereus* infection (*Bacillus cereus*), Bacterial pneumonia (multiple bacteria), Bacterial vaginosis (List of bacterial vaginosis microbiota), *Bacteroides* infection (*Bacteroides* species), Balantidiasis (*Balantidium coli*), Bartonellosis (*Bartonella*), *Baylisascaris* infection (*Baylisascaris* species), BK virus infection (BK virus), Black *piedra* (*Piedraia hortae*), Blastocystosis (*Blastocystis* species), Blastomycosis (*Blastomyces dermatitidis*), Bolivian hemorrhagic fever (Machupo virus), Botulism (and Infant botulism) (*Clostridium botulinum*; Note: Botulism is not an infection by *Clostridium botulinum* but caused by the intake of botulinum toxin), Brazilian hemorrhagic fever (Sabia virus), Brucellosis (*Brucella* species), Bubonic plague (the bacterial family Enterobacteriaceae), *Burkholderia* infection, usually *Burkholderia cepacia* and other *Burkholderia* species, Buruli ulcer (*Mycobacterium ulcerans*), Calicivirus infection (Norovirus and Sapovirus) (Caliciviridae family), Campylobacteriosis (*Campylobacter* species), Candidiasis (Moniliasis; Thrush) (usually *Candida albicans* and other *Candida* species), Capillariasis (Intestinal disease by *Capillaria philippinensis*, hepatic disease by *Capillaria hepatica* and pulmonary disease by *Capillaria aerophila*), Carrion's disease (*Bartonella bacilliformis*), Cat-scratch disease (*Bartonella henselae*), Cellulitis (usually Group A *Streptococcus* and *Staphylococcus*), Chagas Disease (American trypanosomiasis) (*Trypanosoma cruzi*), Chancroid (*Haemophilus ducreyi*), Chickenpox (Varicella *zoster* virus (VZV)), Chikungunya (Alphavirus), *Chlamydia* (*Chlamydia trachomatis*), *Chlamydophila pneumoniae* infection (Taiwan acute respiratory agent or TWAR) (*Chlamydophila pneumoniae*), Cholera (*Vibrio cholerae*), Chromoblastomycosis (usually *Fonsecaea pedrosoi*), Chytridiomycosis (*Batrachochytrium* dendrabatidis), Clonorchiasis (*Clonorchis sinensis*), *Clostridium difficile* colitis (*Clostridium difficile*), Coccidioidomycosis (*Coccidioides immitis* and *Coccidioides posadasii*), Colorado tick fever (CTF) (Colorado tick fever virus (CTFV)), Common cold (Acute viral rhinopharyngitis; Acute coryza) (usually rhinoviruses and coronaviruses), Coronavirus, Creutzfeldt-Jakob disease (CJD) (PRNP), Crimean-Congo hemorrhagic fever (CCHF) (Crimean-Congo hemorrhagic fever virus), Cryptococcosis (*Cryptococcus neoformans*), Cryptosporidiosis (*Cryptosporidium* species), Cutaneous larva migrans (CLM) (usually *Ancylostoma braziliense*; multiple other parasites), Cyclosporiasis (*Cyclospora cayetanensis*), Cysticercosis (*Taenia solium*), Cytomegalovirus infection (Cytomegalovirus), Dengue fever (Dengue viruses (DEN-1, DEN-2, DEN-3 and DEN-4)—Flaviviruses), Desmodesmus infection (Green algae Desmodesmus *armatus*), Dientamoebiasis (*Dientamoeba fragilis*), Diphtheria (*Corynebacterium diphtheriae*), Diphyllobothriasis (*Diphyllobothrium*), Dracunculiasis (*Dracunculus medinensis*), Ebola hemorrhagic fever (Ebolavirus (EBOV)), Echinococcosis (*Echinococcus* species), Ehrlichiosis (*Ehrlichia* species), Enterobiasis (Pinworm infection) (*Enterobius vermicularis*), *Enterococcus* infection (*Enterococcus* species), Enterovirus infection (Enterovirus species), Epidemic typhus (*Rickettsia prowazekii*), Erythema infectiosum (Fifth disease) (Parvovirus B19), Exanthem subitum (Sixth disease) (Human herpesvirus 6 (HHV-6) and Human herpesvirus 7 (HHV-7)), Fasciolasis (*Fasciola hepatica* and *Fasciola gigantica*), Fasciolopsiasis (*Fasciolopsis buski*), Fatal familial insomnia (FFI) (PRNP), Filariasis (Filarioidea superfamily), Food poisoning by *Clostridium perfringens* (*Clostridium perfringens*), Free-living amebic infection (multiple), *Fusobacterium* infection (*Fusobacterium* species), Gas gangrene (Clostridial myonecrosis) (usually *Clostridium perfringens*; other *Clostridium* species), Geotrichosis (*Geotrichum candidum*), Gerstmann-Sträussler-Scheinker syndrome (GSS) (PRNP), Giardiasis (*Giardia lamblia*) Glanders (*Burkholderia mallei*), Gnathostomiasis (*Gnathostoma spinigerum* and *Gnathostoma hispidum*), Gonorrhea (*Neisseria gonorrhoeae*), Granuloma inguinale (Donovanosis) (*Klebsiella granulomatis*), Group A streptococcal infection (*Streptococcus pyogenes*), Group B streptococcal infection (*Streptococcus agalactiae*), *Haemophilus influenzae* infection (*Haemophilus influenzae*) Hand, foot and mouth disease (HFMD) (Enteroviruses, mainly Coxsackie A virus and Enterovirus 71 (EV71)), Hantavirus Pulmonary Syndrome (HPS) (Sin Nombre virus), Heartland virus disease (Heartland virus), *Helicobacter pylori* infection (*Helicobacter pylori*), Hemolytic-uremic syndrome (HUS), *Escherichia coli* O157:H7, O111 and O104:H4, Hemorrhagic fever with renal syndrome (HFRS) (Bunyaviridae family), Hepatitis A (Hepatitis A virus), Hepatitis B (Hepatitis B virus), Hepatitis C (Hepatitis C virus), Hepatitis D (Hepatitis D Virus), Hepatitis E (Hepatitis E virus), Herpes simplex (Herpes simplex virus 1 and 2 (HSV-1 and HSV-2)), Histoplasmosis (*Histoplasma capsulatum*), Hookworm infection (*Ancylostoma duodenale* and *Necator americanus*), Human bocavirus infection (Human bocavirus (HBoV)), Human *ewingii* ehrlichiosis (*Ehrlichia ewingii*), Human granulocytic anaplasmosis (HGA) (*Anaplasma phagocytophilum*), Human metapneumovirus infection, Human metapneumovirus (hMPV), Human monocytic ehrlichiosis (*Ehrlichia chaffeensis*), Human papillomavirus (HPV) infection (Human papillomavirus (HPV)), Human parainfluenza virus infection (Human parainfluenza viruses (HPIV)), Hymenolepiasis (*Hymenolepis nana* and *Hymenolepis diminuta*), Epstein-Barr virus infectious mononucleosis (Mono) (Epstein-Barr virus (EBV)), Influenza (flu) (Orthomyxoviridae family) Isosporiasis (*Isospora belli*), Kawasaki disease (unknown; evidence supports that it is infectious) Keratitis (multiple), *Kingella kingae* infection (*Kingella kingae*), Kuru (PRNP), Lassa fever (Lassa virus), Legionellosis (Legionnaires' disease) (*Legionella pneumophila*), Legionellosis (Pontiac fever) (*Legionella pneumophila*), Leishmaniasis (*Leishmania* species), Leprosy (*Mycobacterium leprae* and *Mycobacterium* lepromatosis), Leptospirosis (*Leptospira species*), Listeriosis (*Listeria monocytogenes*), Lyme disease (Lyme borreliosis) (*Borrelia burgdorferi, Borrelia garinii*, and *Borrelia afzelii*), Lymphatic filariasis (Elephantiasis) (*Wuchereria bancrofti* and *Brugia malayi*), Lymphocytic choriomeningitis (Lymphocytic choriomeningitis virus (LCMV)), Malaria (*Plasmodium* species), Marburg hemorrhagic fever (MHF) (Marburg virus), Measles (Measles virus), Middle East respiratory syndrome (MERS) (Middle East respiratory syndrome coronavirus), Melioidosis (Whitmore's disease) (*Burkholderia pseudomallei*), Meningitis (multiple), Meningococcal disease (*Neisseria meningitidis*), Metagonimiasis (usually *Metagonimus* yokagawai), Microsporidiosis (Microsporidia phylum), Molluscum contagiosum (MC) (Molluscum contagiosum virus (MCV)), Monkeypox (Monkeypox virus), Mumps (Mumps virus), Murine typhus (Endemic typhus) (*Rickettsia typhi*), *Mycoplasma* pneumonia (*Mycoplasma pneumoniae*), Mycetoma (disambiguation) (numerous species of bacteria (Actinomycetoma) and fungi (Eumycetoma)), Myiasis (parasitic dipterous fly larvae), Neonatal conjunctivitis (Ophthalmia neonatorum) (most commonly *Chlamydia trachomatis* and *Neisseria gonorrhoeae*), Norovirus (children and babies) ((New) Variant Creutzfeldt-Jakob disease (vCJD, nvCJD), PRNP), Nocardiosis (usually *Nocardia asteroides* and other *Nocardia* species), Onchocerciasis (River blindness) (*Onchocerca volvulus*), Opisthorchiasis (*Opisthorchis viverrini* and *Opisthorchis felineus*), Paracoccidioidomycosis (South American blastomycosis) (*Paracoccidioides brasiliensis*), Paragonimiasis (usually *Paragonimus westermani* and other *Paragonimus* species), Pasteurellosis (*Pasteurella* species), Pediculosis *capitis* (Head lice) (*Pediculus humanus capitis*), Pediculosis *corporis* (Body lice) (*Pediculus humanus corporis*), Pediculosis *pubis* (Pubic lice, Crab lice) (*Phthirus pubis*), Pelvic inflammatory disease (PID) (multiple), Pertussis (Whooping cough) (*Bordetella pertussis*), Plague (*Yersinia pestis*), Pneumococcal infection (*Streptococcus pneumoniae*), *Pneumocystis* pneumonia (PCP) (*Pneumocystis jirovecii*), Pneumonia (multiple), Poliomyelitis (Poliovirus), *Prevotella* infection (*Prevotella* species), Primary amoebic meningoencephalitis (PAM) (usually *Naegleria fowleri*), Progressive multifocal leukoencephalopathy (JC virus), Psittacosis (*Chlamydophila psittaci*), Q fever (*Coxiella burnetii*), Rabies (Rabies virus), Relapsing fever (*Borrelia hermsii, Borrelia recurrentis*, and other *Borrelia* species), Respiratory syncytial virus infection (Respiratory syncytial virus (RSV)), Rhinosporidiosis (*Rhinosporidium seeberi*), Rhinovirus infection (Rhinovirus), Rickettsial infection (*Rickettsia* species), Rickettsialpox (*Rickettsia akari*), Rift Valley fever (RVF) (Rift Valley fever virus), Rocky Mountain spotted fever (RMSF) (*Rickettsia rickettsii*), Rotavirus infection (Rotavirus), Rubella (Rubella virus), Salmonellosis (*Salmonella* species), SARS (Severe Acute Respiratory Syndrome) (SARS coronavirus), Scabies (*Sarcoptes scabiei*), Schistosomiasis (*Schistosoma* species), Sepsis (multiple), Shigellosis (Bacillary dysentery) (*Shigella* species), Shingles (Herpes *zoster*) (Varicella *zoster* virus (VZV)), Smallpox (Variola) (Variola major or Variola minor), Sporotrichosis (*Sporothrix schenckii*), Staphylococcal food poisoning (*Staphylococcus* species), Staphylococcal infection (*Staphylococcus* species), Strongyloidiasis (*Strongyloides stercoralis*), Subacute sclerosing panencephalitis (Measles virus), Syphilis (*Treponema pallidum*), Taeniasis (*Taenia* species), Tetanus (Lockjaw) (*Clostridium tetani*), Tinea barbae (Barber's itch) (usually *Trichophyton* species), *Tinea capitis* (Ringworm of the Scalp) (usually *Trichophyton tonsurans*), *Tinea corporis* (Ringworm of the Body) (usually *Trichophyton* species), *Tinea* cruris (Jock itch) (usually *Epidermophyton floccosum, Trichophyton rubrum*, and *Trichophyton mentagrophytes*), *Tinea manum* (Ringworm of the Hand) (*Trichophyton rubrum*), *Tinea nigra* (usually *Hortaea werneckii*), *Tinea pedis* (Athlete's foot) (usually *Trichophyton* species), *Tinea unguium* (Onychomycosis) (usually *Trichophyton* species), *Tinea versicolor* (*Pityriasis versicolor*) (*Malassezia* species), Toxocariasis (Ocular Larva Migrans (OLM)) (*Toxocara canis* or *Toxocara cati*), Toxocariasis (Visceral Larva Migrans (VLM)) (*Toxocara canis* or *Toxocara cati*), Trachoma (*Chlamydia trachomatis*), Toxoplasmosis (*Toxoplasma gondii*), Trichinosis (*Trichinella spiralis*), Trichomoniasis (*Trichomonas vaginalis*), Trichuriasis (Whipworm infection) (*Trichuris trichiura*), Tuberculosis (usually *Mycobacterium tuberculosis*), Tularemia (*Francisella tularensis*), Typhoid fever (*Salmonella enterica* subsp. *enterica*, serovar *typhi*), Typhus fever (*Rickettsia*), *Ureaplasma urealyticum* infection (*Ureaplasma urealyticum*), Valley fever (*Coccidioides immitis* or *Coccidioides posadasii*), Venezuelan equine encephalitis (Venezuelan equine encephalitis virus), Venezuelan hemorrhagic fever (Guanarito virus), *Vibrio vulnificus* infection (*Vibrio vulnificus*), *Vibrio parahaemolyticus* enteritis (*Vibrio parahaemolyticus*), Viral pneumonia (multiple viruses), West Nile Fever (West Nile virus), White *piedra* (*Tinea* blanca) (*Trichosporon beigelii*), *Yersinia pseudotuberculosis* infection (*Yersinia pseudotuberculosis*), Yersiniosis (*Yersinia enterocolitica*), Yellow fever (Yellow fever virus), Zygomycosis (Mucorales order (Mucormycosis) and Entomophthorales order (Entomophthoramycosis)) Human immunodeficiency virus [HIV] disease, HIV disease with infectious and parasitic diseases, HIV disease with mycobacterial infection, HIV disease with cytomegaloviral disease, HIV disease with other viral infections, HIV disease with candidiasis, HIV disease with other mycoses, HIV disease with Pneumocystic *carinii* pneumonia, HIV disease with malignant neoplasms, HIV disease with Kaposi's sarcoma, HIV disease with Burkitt's lymphoma, HIV disease with other type's of non-Hodgkin's lymphoma, HIV disease with other malignant neoplasms of lymphoid, hematopoietic and related tissue, HIV disease with multiple malignant neoplasms, HIV disease with other malignant neoplasms, HIV disease with unspecified malignant neoplasm, HIV disease with encephalopathy, HIV disease with lymphoid interstitial pneumonitis, HIV disease with wasting syndrome, HIV disease with multiple diseases classified elsewhere, HIV disease with other conditions, HIV disease Acute HIV infection syndrome, HIV disease with (persistent) generalized lymphadenopathy, HIV disease with hematological and immunological abnormalities, HIV disease with other specified conditions, or Unspecified HIV disease. In some embodiments of the disclosure the infectious disease may be infection with a virus, such as a virus from one of the following families of viruses: a) Adenoviridae family, Such as Adenovirus species; b) Herpesviridae family, Such as Herpes simplex type 1, Herpes simplex type 2, Varicella *zoster* virus, Epstein-barr virus, Human cytomegalovirus, Human herpesvirus type 8 species; c) Papillomaviridae family, Such as Human papillomavirus species; d) Polyomaviridae family, such as BK virus, JC virus species; e) Poxviridae family, Such as Smallpox species: f) Hepadnaviridae family, such as Hepatitis B virus species: g) Parvoviridae family, such as Human bocavirus, Parvovirus B19 species; h) Astroviridae family, such as Human astrovirus species: i) Caliciviridae family, such as Norwalk virus species; j) Flaviviridae family, such as Hepatitis C virus (HCV), yellow fever virus, dengue virus, West Nile virus species; k) Togaviridae family, such as Rubella virus species; l) Hepeviridae family, such as Hepatitis E virus species; m) Retroviridae family, such as Human immunodeficiency virus (HIV) species; n) Orthomyxoviridaw family, such as Influenza virus species; o) Arenaviridae family, such as Guanarito virus, Junin virus, Lassa virus, Machupo virus, and/or Sabia virus species; p) Bunyaviridae family, Such as Crimean-Congo hemorrhagic fever virus species; q) Filoviridae family, such as Ebola virus and/or Mar burg virus species; Paramyxoviridae family, Such as Measles virus, Mumps virus, Parainfluenza virus, Respiratory syncytial virus, Human metapneumovirus, Hendra virus and/or Nipah virus species; r) Rhabdoviridae genus, such as Rabies virus species; s) Reoviridae family, such as Rotavirus, Orbivirus, Coltivirus and/or Banna virus species.

In some embodiments of the disclosure, the microbial disease may not be one of the above recited infectious diseases.

In some embodiments, the microbial disease may be a disease caused by infection with an influenza A (Flu A) virus. In some embodiments the influenza virus can be an avian or swine-origin pandemic influenza virus, for example, H5N1, H7N3, H7N7, H7N9 and H9N2 (avian subtypes) or H1N1, H1N2, H2N1, H3N1, H3N2, or H2N3 (swine subtypes).

In some embodiments of the disclosure, the microbial disease may be HIV, such as residual HIV disease, herpes, hepatitis or human papilloma virus. In other embodiments, the microbial disease may be a disease resulting from infection with a coronavirus, for example COVID-19 (coronavirus 2019; the disease caused by severe acute respiratory syndrome coronavirus 2, SARS-CoV-2).

In the methods of the disclosure the ICAM3 modulating agents may treat "microbial disease" (also termed "infectious disease") by any of the mechanisms outlined elsewhere herein—in particular via the production and mobilization of novel immune cell populations, including novel populations of Natural Killer T (NKT) cells, from the spleen, thymus, or bone marrow into the circulation. For example, mobilized NKT cells may treat the microbial disease via engulfing and killing the infectious organism, activating other innate and adaptive immune cells, recruiting other immune cells to the site of infection (e.g. an organ infected by a virus), or by depleting immune cells infected by the virus (e.g. monocytes activated by COVID-19). In this context, "treat" means to exert a beneficial therapeutic effect in the subject, which can be any overall clinical benefit derived from the methods of the disclosure. This overall clinical benefit can be any of, for example: reduced fever, reduced diarrhea, reduced coughing, reduced muscle aches, reduced fatigue, reduced CRP, reduced time on ventilator, reduced need for extra oxygen, reduced organ damage after recovery.

Administration Routes

As used herein, the term "administering" refers to the physical introduction of an agent to a subject, using any of the various methods and delivery systems known to those skilled in the art. Exemplary routes of administration for the agents disclosed herein include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. In some embodiments, the agents disclosed herein may be administered via a non-parenteral route, e.g., orally. Other non-parenteral routes include a topical, epidermal, or mucosal route of administration, for example, intranasally, vaginally, rectally, sublingually or topically.

The phrase "systemic injection" as used herein non-exclusively relates to intravenous, intraperitoneally, subcutaneous, via nasal submucosa, lingual, via bronchoscopy, intravenous, intra-arterial, intra-muscular, intro-ocular, intra-striatal, subcutaneous, intradermal, by dermal patch, by skin patch, by patch, into the cerebrospinal fluid, into the portal vein, into the brain, into the lymphatic system, intrapleural, retro-orbital, intra-dermal, into the spleen, intralymphatic, among others.

The term 'site of injection' as used herein non-exclusively relates to intra-tumor, or intra-organ such as the kidney or liver or pancreas or heart or lung or brain or spleen or eye, intra-muscular, intro-ocular, intra-striatal, intradermal, by dermal patch, by skin patch, by patch, into the cerebrospinal fluid, into the brain, among others.

In some preferred embodiments of the disclosure, the glucocorticoid-receptor modulating agents may be administered orally.

In some embodiments of the disclosure, the route of administration for the agents and cells disclosed herein may not be one or more of the above recited routes.

Cell Types

Dendritic cells (DCs) are bone marrow-derived leukocytes, and are the most potent antigen-presenting cells of the mammalian immune system. DCs exert immune-surveillance for exogenous and endogenous antigens and the later activation of naive T lymphocytes giving rise to various immunological responses. DCs are sentinel cells responsible for the recognition of pathogens and signals of tissue damage, which induces their migration to lymphoid organs to carry out the activation of different subsets of T, natural killer (NK), NKT, and B lymphocytes. Mature phenotype cDC are characterized by an increase in MHCII, CD80, CD86, and CD40. Dendritic cells are frequently classified into conventional dendritic cell (cDC) and plasmacytoid dendritic cell (pDC) subsets. Dendritic cells exist primarily in two basic functional states: "immature" and "mature". Activation (maturation) of dendritic cells turns on metabolic, cellular, and gene transcription programs allowing DC to migrate from peripheral tissues to T-dependent areas in secondary lymphoid organs, where T lymphocyte-activating antigen presentation may occur (Patente et al, 2018; hereby incorporated by reference in its entirety). The main function of dendritic cells is to process antigen material and present it on the cell surface to T cells thus initiating adaptive immune responses. Dendritic cells also produce polarizing cytokines that promote pathogen-specific effector T cell differentiation and activation, and can promote self-tolerance by secreting tolerogenic cytokines that induce the differentiation of regulatory T cells. The DCs induced by high dose glucocorticoids, and which may be induced by the methods of the disclosure may express CD11b to a very high level ("CD11b-very-high dendritic cells").

T cells are a type of lymphocyte that play a key role in the immune response. T cells are distinguished from other types of lymphocytes by the presence of T-cell receptors on their cell surface. T-cell receptors (TCRs) are responsible for recognizing fragments of antigen bound to major histocompatibility complex (MHC) molecules, and are heterodimers of two different protein chains. In humans, in 95% of T cells the TCR consists of an alpha ($\alpha$) chain and a beta ($\beta$) chain (encoded by TRA and TRB, respectively), whereas in 5% of T cells the TCR consists of gamma and delta ($\gamma/\delta$) chains (encoded by TRG and TRD, respectively). This ratio changes in diseased states (such as leukemia). In contrast to MHC-restricted alpha beta T cells, gamma delta T cells do not require antigen processing and major-histocompatibility-complex (MHC) presentation of peptide epitopes for activation, although some recognize MHC class Ib molecules. Some gamma delta T cells recognise markers of cellular stress resulting from infection or tumorigenesis. Gamma delta T cells are also believed to have a role in recognition of lipid antigens. The T cells induced by high dose glucocorticoids, and which may be induced by the methods of the disclosure may express CD3 to a very high level ("CD3-very-high"). The T cells may express both CD4 and CD8.

Natural Killer T Cells (NKTs) are a heterogeneous group of T cells that share properties of both T cells and natural killer (NK) cells. In contrast to conventional T cells, NKTs are functionally mature when they exit the thymus, primed for rapid cytokine production. NKTs can directly kill cancer cells and tumor microenvironment macrophages, rapidly produce and release immune activating cytokines such as IFNgamma and IL-4, and activate other immune cells such as dendritic cells (DCs), NK cells, and B and T lymphocytes.

The authors have found a novel type of NKT cells, denoted AVM_NKT, which homes remarkably well to diseased tissues such as tumors in tumor killing models used to show efficacy of checkpoint inhibitors. AVM_NKT are mobilized only after AVM0703 treatment, as opposed to other NK and NKT which circulate continuously, therefore AVM_NKT numbers are unlimited in practice. Normal NK and NKT cells have been shown to reduce Influenza A mediated inflammation and disease severity, and CD11b+ DC have been implicated in protection against Respiratory Syncytial Virus and Influenza A (H1N1). The NKT cells induced by high dose glucocorticoids, and which may be induced by the methods of the disclosure may express CD3 to a very high level ("CD3-very-high"), and: may express CD4, CD8, CD45, CD49b (CD56 in humans), CD62L, NK1.1, Ly6G, Sca1, and/or TCR gamma/delta; and/or, may not express: C-kit, B220, FoxP3, and/or TCR alpha/beta.

Determining Cell Marker Expression Levels

Markers expressed by NKT cells, T cells or DCs induced by the methods of the disclosure can be determined by reference to the level of marker expression by a typical NKT cell, T cell or DC population (respectively), e.g. taken from the patient prior to treatment. Where the expression level is said to be "very high" this can denote 50%, 60%, 70%, 80%, 90% or 100% higher level expression of the marker compared to the respective typical cell population. Expression levels may be determined by flow cytometry.

The features disclosed in the foregoing description, or in the following claims, or in the accompanying drawings, expressed in their specific forms or in terms of a means for performing the disclosed function, or a method or process for obtaining the disclosed results, as appropriate, may, separately, or in any combination of such features, be utilised for realising the invention in diverse forms thereof.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

For the avoidance of any doubt, any theoretical explanations provided herein are provided for the purposes of improving the understanding of a reader. The authors do not wish to be bound by any of these theoretical explanations.

Any section headings used herein are for organizational purposes only and are not to be construed as limiting the subject matter described.

Throughout this specification, including the claims which follow, unless the context requires otherwise, the word "comprise" and "include", and variations such as "comprises", "comprising", and "including" will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment. The term "about" in relation to a numerical value is optional and means for example +/−10%.

EXAMPLES

The following examples demonstrate that high dose glucocorticoids are able to bind to a receptor (ICAM3) that is distinct from the published intracellular or transmembrane glucocorticoid receptors, and which is highly expressed on lymphocytes, monocytes and neutrophils, as well as on cancer cell types such as melanoma and osteosarcoma.

These examples also demonstrate that high dose glucocorticoids are able to exert a concentration dependent, direct killing effect on these cancer cell types—an effect that is likely mediated by binding of glucocorticoids to ICAM3 causing the ICAM3-expressing cell becoming marked for attack by other lymphocytes such as NKT cells and CD8+ T cells. ICAM3 shedding may also occur following glucocorticoid binding, further stimulating an immune response against these cell types High doses of glucocorticoids, and other ICAM3 modulating agents thus represent a promising therapy for use in the treatment of cancer and diseases mediated by immune cells such as lymphocytes.

Acute high dose dexamethasone may also be referred to herein as Dex, AugmenStem™, PlenaStem™ or AVM0703.

Example 1—Acute High Dose Dexamethasone Binds to Intracellular Adhesion Molecule 3 (ICAM3

Figure 1A:
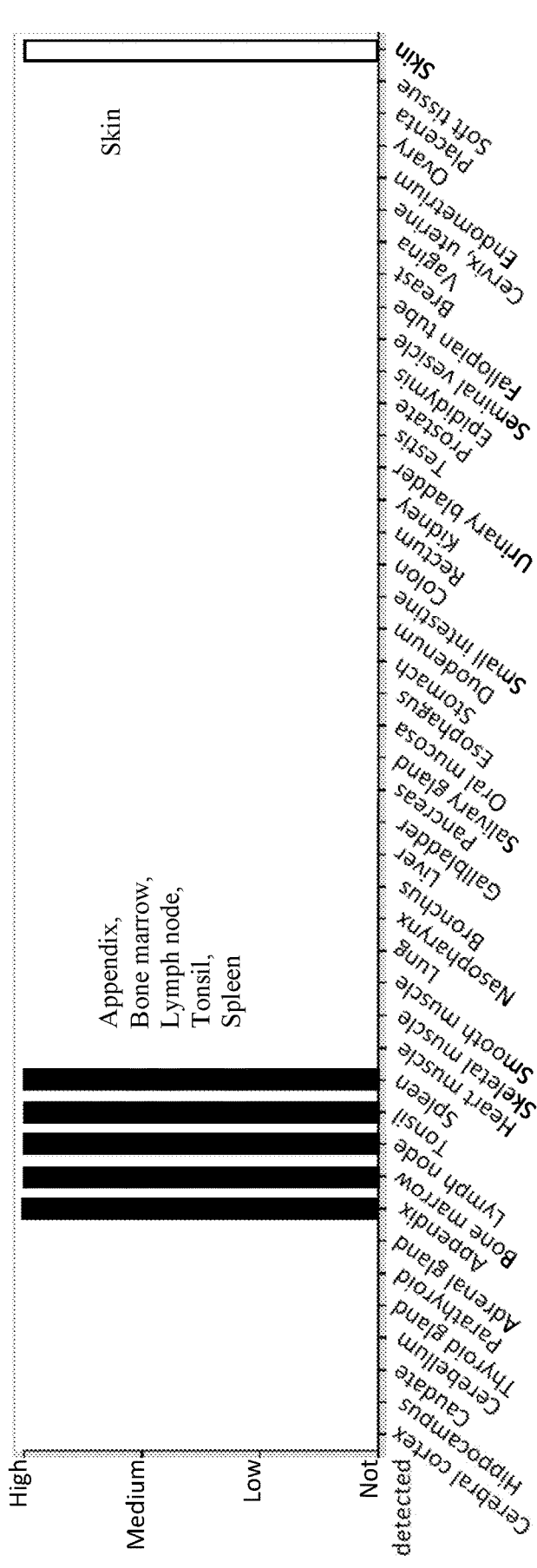
FIG. 1A-1B. 1A: AVM0703 Receptor (ICAM3) protein expression levels in various organs from the Human Proteome Project. Expression is highly observed on hematopoietic/immune organs (all examined) and skin which contains high concentrations of immune cells. 1B: From the Fantom5 Dataset, measuring ICAM3 RNA expression, lung expresses moderate levels of ICAM3. RNA is also expressed by multiple myeloid and lymphoid lineage cell lines, including HEL, HL-60, HMC-1, K-562, NB-4, THP-1, U-937, Daudi, HDLM-2, Laspas_707, MOLT-4, REH, RPMI-8226, U-266/70, U-266/84, and U-698 cell lines (data not shown).
Figure 1B:

The present authors have identified that high dose glucocorticoids bind a receptor that is distinct from the published intracellular or transmembrane glucocorticoid receptors. When investigating high concentrations of glucocorticoids as a pre-conditioning regime before stem cell therapy or cellular immunotherapies (see, for example, WO2018/183927), the present authors surprisingly observed a degree of cancer cell killing in lymphoma models when high concentrations of glucocorticoids were administered in the absence of cellular therapy. Initial analysis of protein/RNA expression levels of the receptor mediating this effect in various organs found that it is highly expressed on hematopoietic organs and skin (see FIG. 1), as well as by lymphomas (see FIG. 2) and paediatric cancers (see FIG. 3).

Subsequent investigation of the expression profile of proteins expressed by lymphoma cells lines and the biological responses observed by the authors in naïve and tumor bearing mice identified the receptor mediating the direct cancer killing effect of high dose glucocorticoids as ICAM3. The restricted expression profile of ICAM3 gives AVM0703 and other acute high dose glucocorticoid treatments a preferred safety profile over other chemotherapeutics.

Example 2—AVM0703 Receptor (ICAM3) is Expressed by U2 OS Osteosarcoma Cells and Mediates AVM0703 Induced In Vitro Apoptosis of U2 OS Cells in a Concentration-Dependent Manner As shown in FIG. 4, the AVM0703 Receptor (ICAM3) is expressed by U2 OS osteosarcoma cells. In vitro administration of acute high dose dexamethasone triggered apoptosis of these cells in a concentration dependent manner (FIG. 5). Dexamethasone base doses that induced apoptosis include 50, 100, 175, and 250 μM.

Consistent with these results, acute high dose dexamethasone was found to prevent A20 B lymphoma and B16F10 melanoma growth in vivo.

Example 3—Absent Ex Vivo Effect of High Concentration Dexamethasone on Whole Blood or Splenocytes Ex vivo whole blood or isolated splenocytes had no response to AVM0703 or dexamethasone base at concentrations between 100 uM up to 500 uM, the equivalent concentrations attained at peak in vivo dosing around Human Equivalent Dose (HED) 6 mg/kg and higher. These data demonstrate that at the doses preferred for cancer and infectious disease treatments (HED 6 mg/kg up to 30 mg/kg) AVM0703 does not activate glucocorticoid receptors nor the ICAM3 receptor directly expressed on lymphocytes, monocytes or neutrophils. The profound in vivo activity that is observed in naïve mice and in cancer models must therefore be mediated through the mobilized supercharged Natural Killer T cells, T cells and dendritic cells after AVM0703 HED 6 mg/kg and higher.

The incubation conditions shown in Table 2 were investigated.

TABLE 2

| | | | Incubation conditions | | | | |
|---|---|---|---|---|---|---|---|
| Study No. | Cell Type | Vol. (μL) | Container | Temp (° C.) | CO$_2$ (%) | Agitation | Time-point (hr) |
| 6 | Whole Blood | 300 | 1.5 mL microcentrifuge tube | Room temperature | Atmospheric | None | 16 |
| 24 | Whole Blood | 400 | 24-well plate | Room temperature | Atmospheric | Orbital | 16 |
| | Spleno-cytes | 500 | 24-well plate | 37 | 3% | None | 4 |
| Venetoclax 1 | Whole blood | | 1.5 mL microcentrifuge tube | Room temperature | Atmospheric | None | 2, 22 |
| Glucocorticoid Comparison | Whole blood | | 1.5 mL microcentrifuge tube | Room temperature | Atmospheric | None | Overnight |

Results: Whole Blood (Study 6)

Samples were treated in triplicate with either 500 μM dexamethasone base, 50 RU486 (a steroid receptor antagonist), or 1% DMSO as control. A non-significant increase in neutrophils induced by RU486 treatment. Other immune cells types; lymphocytes, monocytes, eosinophils, basophils; displayed no change in numbers with dexamethasone base or RU486 treatment. The data indicates that dexamethasone base alone in whole blood does not induce the lymphocyte-killing activity seen in in vivo experiments. RU486 alone also has no killing activity on lymphocytes and can be given in combination without impacting lymphocyte levels.

Results: Splenocytes (Study 24)

Splenocytes were cultured for 16 hours prior to assay execution. Flow cytometry was performed at four hours after dexamethasone base addition, and the results are shown in FIG. 6. After 4 hours, dexamethasone base appears to have direct killing activity at concentrations lower than 100 but does not trigger cell death above 100 μM.

The results of Study 6 and 24 suggest that the mechanism of action is different between low and high concentrations of dexamethasone base, where high doses have no activity on splenocytes. This is in contrast to previous in vivo data, where the weight of the spleen is sharply reduced by AVM0703 dosing. (See WO2018/183927 and WO2020/072713; both incorporated by reference in their entirety, for discussion of these in vivo effects.) The discrepancy between ex vivo and in vivo indicates that a different mechanism of action is occurring in vivo compared to ex vivo.

Results: Venetoclax 1

No significant difference was found for any measured parameter of CBC when whole blood was incubated with Placebo, DMSO, AVM0703 at 500 μM alone, or combined with venetoclax at 3 μM. Particularly, there is no significant effect on white blood cells. Lymphocytes, monocytes, and neutrophils do not exhibit the lymphodepletion or ablation observed in vivo. Thus, these results indicate that cells in whole blood are not influenced by AVM0703 via GCR activation (venetoclax increases glucocorticoid sensitivity).

Results; Ex Vivo Glucocorticoid Comparison

To determine whether the absence of ex vivo effect on monocytes, lymphocytes, and neutrophils was due to the concentration of dexamethasone base of 100 uM to 500 uM, or whether the different excipients in AVM0703 could be contributing we compared ex vivo treatment followed by CBC analysis among AVM0703 compared with other commercially available Dexamethasone Phosphate. There were no noticeable differences between the different formulations, indicating that it is the concentrations of dexamethasone base that have an unexpected ex vivo effect; i.e. the surprising lack of ex vivo cell death.

Example 4—ICAM-3 Detection in C56BL/6 Mouse Tissue

Five naïve male C57BL/6 mice aged 24 weeks obtained from Taconic Bioscience (Germantown, NY) were euthanized via exsanguination and perfusion. Mice were anesthetized with isoflurane gas and injected IP with 90 U/mL heparin and 5% avertin. Blood was drawn via cardiac puncture and transferred immediately into EDTA-lined microtainer tubes. The mice were perfused with 10 mL of 5 U/mL heparin/PBS via the left ventricle. For proper drainage, a small 2-3 mm incision was made in each lobe of the liver. Spleen and thymus were harvested and transferred to ice cold PBS until further processing.

To avoid animal to animal variability, spleen or thymus from each mouse were pooled together as single cell suspensions following maceration through a 70 μm filter with 1×HBSS containing 2% FBS. Mouse whole blood was pooled together in a 5 mL EDTA-lined tube and RBC lysed with a 1:10 ratio of BD FACs lysis buffer. Splenocytes were RBC lysed with a 1:9 ratio of ammonium chloride. All cell suspensions were washed twice with ice cold PBS prior to whole cell lysis with a modified RIPA buffer.

Cell lysates were quantified via Pierce™ Rapid Gold BCA Protein Assay kit (ThermoFisher Scientific) and a Spectramax i3 plate reader (Molecular Devices). Cell lysates were reduced with 40 mM DTT for 30 minutes at room temperature before being analyzed on Wes, a microfluidic, high-throughput, capillary-based Western assay system (Protein Simple). Samples were run against a monoclonal rabbit anti-human ICAM3 primary antibody at varying concentrations to establish the point of signal saturation. Spleen and thymus tissue lysates were also run at varying sample concentrations to establish linearity of the assay. Due to low protein concentration, blood lysate was run at a single low-sample concentration.

A no primary antibody control indicated no cross reactivity between sample and secondary antibody. A no sample control demonstrated that the primary antibody was clean and produced no signal in the absence of sample. Human PBMCs, a known expressor of ICAM3, were lysed and reduced under the same conditions and used as a positive control.

Results—ICAM3 is Expressed in Mouse Thymus, Spleen, and Blood

ICAM-3 is a heavily glycosylated protein which can lead to variations in its molecular weight and/or presentation of multiple protein bands on a western blot as it detects variants. The molecular weight of the protein alone is 59.5 KDa. However, due to post-translational modifications, we expect to see ICAM-3 within the 110-160 KDa molecular weight range.

Based on this information, the western blot results for mouse thymus and spleen were conclusive. As shown in FIG. 7, a clear band was seen at 144 KDa for mouse thymus lysates. Human PBMCs show the same band at ~145 KDa along with a smaller band at 62 Kda.

As shown in FIG. 8, in the mouse spleen lysates 2 bands are detected at 145 KDa and 115 KDa. At the highest sample concentration and lowest primary antibody dilution, a much fainter band at ~62 KDa is also seen in mouse spleen. The protein band at 145 KDa and 62 KDa in mouse spleen is matched by the human PBMCs which are serving as a positive control.

Experimental issues with the blood lysis resulted in blood lysates with very low concentration of protein. These mouse blood experiments will therefore be repeated to obtain higher sample concentration to run on the western blot. However, even at the very low sample concentrations used, results are promising—as shown in FIG. 9, at the lowest primary antibody dilution, a faint band is seen in mouse blood at ~149 KDa which matches the protein band size seen in human PBMCs. Further experiments are underway to acquire conclusive results.

REFERENCES

A number of publications are cited above in order to more fully describe and disclose the invention and the state of the art to which the invention pertains. Each reference is hereby incorporated by reference in its entirety. Full citations for these references are provided below:

Mato et al, Haematologica. 2018 September; 103(9):1511-1517;

Kadri et al, Blood Adv. 2017 May 2; 1(12):715-727;

Mato et al, Blood. 2016 Nov. 3; 128(18):2199-2205;

Hua, Front Pharmacol. 2013 Oct. 4; 4:127;

Shen et al, Cancer Lett. 2018 May 28; 422: 29-43;

Schroder et al, J Cancer Res Clin Oncol. 2011 August; 137(8):1193-201

Juan et al, Allergy. 1999 December; 54(12):1293-8;

Choi et al, Cytotherapy. (2017) October; 19(10):1248-1250;

Fauci et al, J. Immunol. (1976) 118, 598;

Gregory & Pound, Apoptosis. 2010 September; 15(9):1029-49;

Moffatt et al, J Immunol. 1999 Jun. 1; 162(11):6800-10;

Torr et al, Cell Death Differ. 2012 April; 19(4): 671-679;

Patente et al; Front Immunol. 2018; 9: 3176

For standard molecular biology techniques, see Sambrook, J., Russel, D. W. Molecular Cloning, A Laboratory Manual. 3 ed. 2001, Cold Spring Harbor, New York: Cold Spring Harbor Laboratory Press

Statements of Disclosure

The following numbered statements, outlining aspects of the present disclosure, are part of the description.

101. A method of treating cancer or a lymphocyte-mediated disease or a microbial disease in a subject, the method comprising administering a therapeutically effective amount of an ICAM-3 modulating agent to the subject.

ICAM-3 Modulating Agent

102. The method of statement 101, wherein the ICAM-3 modulating agent is an ICAM3 activator.

103. The method of statement 101 or 102, wherein the ICAM3 modulating agent is a glucocorticoid-receptor (GR) modulating agent.

104. The method of statement 103, wherein the glucocorticoid-receptor (GR) modulating agent acts as an ICAM3 activator.

105. The method of statement 103 or 104, wherein the glucocorticoid-receptor (GR) modulating agent is a glucocorticoid, optionally wherein the glucocorticoid is selected from the group consisting of: dexamethasone, hydrocortisone, methylprednisolone, prednisone, prednisolone, prednylidene, cortisone, budesonide, betamethasone, flumethasone, ciclesonide, and beclomethasone.

106. The method according to statement 105, wherein the glucocorticoid is selected from the group consisting of: dexamethasone, betamethasone, and methylprednisone, preferably wherein the glucocorticoid is dexamethasone or betamethasone.

107. The method according to any one of statements 105-106, wherein the glucocorticoid is selected from the group consisting of dexamethasone base, dexamethasone sodium phosphate, dexamethasone hemisuccinate, dexamethasone sodium succinate, dexamethasone succinate, dexamethasone isonicotinate, dexamethasone-21-acetate, dexamethasone phosphate, dexamethasone-21-phosphate, dexamethasone tebutate, dexamethasone-17-valerate, dexamethasone acetate monohydrate, dexamethasone pivalate, dexamethasone palmitate, dexamethasone-21-palmitate, dexamethasone dipropionate, dexamethasone propionate, dexamethasone acetate anhydrous, dexamethasone-21-phenylpropionate, dexamethasone-21-sulfobenzoate, dexamethasone hemo-sulfate, dexamethasone sulfate, dexamethasone beloxil, dexamethasone acid, dexamethasone acefurate, dexamethasone carboximide, dexamethasone cipecilate, dexamethasone 21-phosphate disodium salt, dexamethasone mesylate, dexamethasone linoleate, dexamethasone glucoside, dexamethasone glucuronide, dexamethasone iodoacetate, dexamethasone oxetanone, carboxymethylthio-dexamethasone, dexamethasonebisethoximes, dexamethasone epoxide, dexamethasonelinolelaidate, dexamethasone methylorthovalerate, dexamethasone spermine, 6-hydroxy dexamethasone, dexamethasone tributylacetate, dexamethasone aspartic acid, dexamethasone galactopyranose, dexamethasone hydrochloride, hydroxy dexamethasone, carboxy dexamethasone, desoxy dexamethasone, dexamethasone butazone, dexamethasone cyclodextrin, dihydro dexamethasone, oxo dexamethasone, propionyloxy dexamethasone, dexamethasone galactodie, dexamethasone isonicotinate, dexamethasone sodium hydrogen phosphate, dexamethasone aldehyde, dexamethasone pivlate, dexamethasone tridecylate, dexamethasone crotonate, dexamethasone methanesulfonate, dexamethasone butylacetate, dehydro dexamethasone, dexamethasone Isothiocyanatoethyl)Thioether, dexamethasone bromoacetate, dexamethasone hemiglutarate, deoxy dexamethasone, dexamethasone chlorambucilate, dexamethasone melphalanate, formyloxy dexamethasone, dexamethasone butyrate, dexamethasone laurate, dexamethasone acetate, and any combination treatment that contains a form of dexamethasone.

108. The method according to statement 107, wherein the dexamethasone is dexamethasone sodium phosphate.

Dose

109. The method according to any preceding statement, wherein the ICAM3 modulating agent is administered at a dose sufficient to block the signalling cascades caused by ICAM3 activation.

110. The method according to any preceding statement, wherein the ICAM3 modulating agent is administered at a dose sufficient to cause ICAM3 shedding from the surface of a cell into the extracellular space.

111. The method according to any preceding statement, wherein the ICAM3 modulating agent is administered at a dose sufficient to cause ICAM3 expressing cells to be marked for attack by immune cells.

112. The method according to any one of statements 105-111, wherein the glucocorticoid is administered at a dose equivalent to about:

i) at least 6-12 mg/kg human equivalent dose (HED) of dexamethasone base;

ii) at least 6 mg/kg human equivalent dose (HED) of dexamethasone base;

iii) at least 12 mg/kg human equivalent dose (HED) of dexamethasone base;

iv) at least 15 mg/kg human equivalent dose (HED) of dexamethasone base;

v) at least 18 mg/kg human equivalent dose (HED) of dexamethasone base;

vi) at least 24 mg/kg human equivalent dose (HED) of dexamethasone base;

vii) 15 mg/kg human equivalent dose (HED) of dexamethasone base;

viii) 24 mg/kg human equivalent dose (HED) of dexamethasone base;

ix) 30 mg/kg human equivalent dose (HED) of dexamethasone base;

x) 45 mg/kg human equivalent dose (HED) of dexamethasone base; or xi) a human equivalent dose (HED) of dexamethasone base taking a value in mg/kg from a range of mg/kg values, wherein said range is bound by two of the mg/kg values set forth in parts i) to x) above.

113. The method according to any one of statements 105-112, wherein the glucocorticoid is administered as a single acute dose, or as a total dose given over about a 72 hour period.

114. The method according to any one preceding statement, wherein the method comprises administering one or more further doses of an ICAM-3 modulating agent to the subject.

115. The method according to statement 114, wherein the one or more further doses are administered:

i) between 24 hours and 120 hours after a preceding administration;

ii) between 24 hours and 48 hours after a preceding administration;

iii) between 72 hours and 120 hours after a preceding administration;

iv) every 24, 48, 72, 96, 120, 144, or 168 hours after a first administration;

v) once every two weeks after a first glucocorticoid administration;

vi) once monthly after a first administration; or vii) twice weekly after a first administration.

Subject

116. The method according to any one of statements 101-115, wherein the subject is mammalian, preferably wherein the subject is human.

117. The method according to any one of statements 101-116, wherein the subject has, is suspected of having, or has been diagnosed with cancer or a lymphocyte-mediated disease or a microbial disease.

Cancer

118. The method of any preceding statement, wherein the lymphocyte-mediated disease is cancer.

119. The method of any preceding statement, wherein the cancer is a lymphoma, melanoma, or osteosarcoma.

120. The method of statement 119, wherein the cancer is lymphoma, preferably a germinal cell lymphoma, B cell lymphoma, T cell lymphoma, or non Hodgkin lymphoma.

Lymphocyte-Mediated Disease

121. The method of any one of statements 101-117, wherein the lymphocyte-mediated disease is an allergic disease such as asthma, or an autoimmune disease.

Mechanism

122. The method of any preceding statement, wherein the ICAM3 modulating agent induces cell death of ICAM3 expressing cells by binding to ICAM3.

123. The method of any preceding statement, wherein the ICAM3 modulating agent induces apoptosis of ICAM3 expressing cells by binding to ICAM3.

124. The method according to any preceding statement, wherein the ICAM3 modulating triggers (activates) cell apoptotic pathways.

125. The method according to any preceding statement, wherein the ICAM3 modulating agent causes ICAM3 shedding from the surface of a cell into the extracellular space.

126. The method according to any preceding statement, wherein the ICAM3 modulating agent causes ICAM3 expressing cells to be marked for attack by immune cells.

127. The method according to any preceding statement, wherein the ICAM3 modulating agent triggers or supports an effective immune response against the ICAM3 expressing cells.

128. The method according statement 127, wherein the effective immune response involves the induction and/or mobilisation of a population of NKT cells that are characterized in that they expresses CD3, and:

i) express CD4, CD8, CD45, CD49b (CD56 in humans), CD62L, NK1.1, Ly6G, Sca1, and/or TCR gamma/delta; and/or ii) do not express: C-kit, B220, FoxP3, and/or TCR alpha/beta.

129. The method according to statement 127 or 128, wherein the effective immune response involves the induction and/or mobilisation of a population of T cells that express CD3 to a very high level ("CD3-very-high").

130. The method according to any one of statements 127-129, wherein the effective immune response involves the induction and/or mobilisation of a population of dendritic cells (DCs) that express CD11b to a very high level ("CD11b-very-high dendritic cells").

131. An ICAM3 modulating agent for use in a method according to any one of statements 101-130.

132. A glucocorticoid for use in a method according to any one of statements 101-130.

133. Use of an ICAM3 modulating agent for the manufacture of a medicament for use in a method according to any one of statements 101-130.

134. Use of a glucocorticoid for the manufacture of a medicament for use in a method according to any one of statements 101-130.

201. A method of treating cancer or a lymphocyte-mediated disease or a microbial disease in a subject, the method comprising administering a therapeutically effective amount of a pharmaceutical composition comprising a glucocorticoid to the subject, wherein the glucocorticoid induces apoptosis of ICAM3 expressing cancer cells or lymphocytes by binding to ICAM3.

202. A pharmaceutical composition comprising a glucocorticoid, for use in a method of treating cancer or a lymphocyte-mediated disease or a microbial disease in a subject, wherein the method of treating comprises administering a dose of the pharmaceutical composition to the subject, and wherein the glucocorticoid induces apoptosis of ICAM3 expressing cancer cells or lymphocytes by binding to ICAM3.

203. A pharmaceutical composition comprising a glucocorticoid, for use in a method of treating cancer or a lymphocyte-mediated disease or a microbial disease in a subject, wherein the method of treating is a method according to any one of statements 101-130.

301. A method of killing an ICAM3 expressing cell, the method comprising contacting the ICAM3 expressing cell with a glucocorticoid receptor modulating agent.

302. The method of statement 301, wherein the glucocorticoid-receptor (GR) modulating agent is a glucocorticoid, optionally wherein the glucocorticoid is selected from the group consisting of: dexamethasone, hydrocortisone, methylprednisolone, prednisone, prednisolone, prednylidene, cortisone, budesonide, betamethasone, flumethasone, ciclesonide, and beclomethasone.

303. The method according to statement 302, wherein the glucocorticoid is selected from the group consisting of: dexamethasone, betamethasone, and methylprednisone, preferably wherein the glucocorticoid is dexamethasone or betamethasone.

304. The method according to any one of statements 302-303, wherein the glucocorticoid is selected from the group consisting of dexamethasone base, dexamethasone sodium phosphate, dexamethasone hemisuccinate, dexamethasone sodium succinate, dexamethasone succinate, dexamethasone isonicotinate, dexamethasone-21-acetate, dexamethasone phosphate, dexamethasone-21-phosphate, dexamethasone tebutate, dexamethasone-17-valerate, dexamethasone acetate monohydrate, dexamethasone pivalate, dexamethasone palmitate, dexamethasone-21-palmitate, dexamethasone dipropionate, dexamethasone propionate, dexamethasone acetate anhydrous, dexamethasone-21-phenylpropionate, dexamethasone-21-sulfobenzoate, dexamethasone hemo-sulfate, dexamethasone sulfate, dexamethasone beloxil, dexamethasone acid, dexamethasone acefurate, dexamethasone carboximide, dexamethasone cipecilate, dexamethasone 21-phosphate disodium salt, dexamethasone mesylate, dexamethasone linoleate, dexamethasone glucoside, dexamethasone glucuronide, dexamethasone iodoacetate, dexamethasone oxetanone, carboxymethylthio-dexamethasone, dexamethasonebisethoximes, dexamethasone epoxide, dexamethasonelinolelaidate, dexamethasone methylorthovalerate, dexamethasone spermine, 6-hydroxy dexamethasone, dexamethasone tributylacetate, dexamethasone aspartic acid, dexamethasone galactopyranose, dexamethasone hydrochloride, hydroxy dexamethasone, carboxy dexamethasone, desoxy dexamethasone, dexamethasone butazone, dexamethasone cyclodextrin, dihydro dexamethasone, oxo dexamethasone, propionyloxy dexamethasone, dexamethasone galactodie, dexamethasone isonicotinate, dexamethasone sodium hydrogen phosphate, dexamethasone aldehyde, dexamethasone pivlate, dexamethasone tridecylate, dexamethasone crotonate, dexamethasone methanesulfonate, dexamethasone butylacetate, dehydro dexamethasone, dexamethasone Isothiocyanatoethyl)Thioether, dexamethasone bromoacetate, dexamethasone hemiglutarate, deoxy dexamethasone, dexamethasone chlorambucilate, dexamethasone melphalanate, formyloxy dexamethasone, dexamethasone butyrate, dexamethasone laurate, dexamethasone acetate, and any combination treatment that contains a form of dexamethasone.

305. The method according to statement 304, wherein the dexamethasone is dexamethasone sodium phosphate.

306. The method according to any preceding statement, wherein the glucocorticoid-receptor (GR) modulating agent is administered at a dose sufficient to activate the signalling cascades caused by ICAM3 activation.

307. The method according to any preceding statement, wherein the glucocorticoid-receptor (GR) modulating agent is administered at a dose sufficient to block the signalling cascades caused by ICAM3 activation 308. The method according to any preceding statement, wherein the glucocorticoid-receptor (GR) modulating agent is administered at a dose sufficient to cause ICAM3 shedding from the surface of a cell.

309. The method according to any preceding statement, wherein the glucocorticoid-receptor (GR) modulating agent is administered at a dose sufficient to cause ICAM3 expressing cells to be marked for attack by immune cells.

310. The method according to any preceding statement, wherein the glucocorticoid-receptor (GR) modulating agent is administered at a dose equivalent to about:

i) at least 6-12 mg/kg human equivalent dose (HED) of dexamethasone base;

ii) at least 6 mg/kg human equivalent dose (HED) of dexamethasone base;

iii) at least 12 mg/kg human equivalent dose (HED) of dexamethasone base;

iv) at least 15 mg/kg human equivalent dose (HED) of dexamethasone base;

v) at least 18 mg/kg human equivalent dose (HED) of dexamethasone base;

vi) at least 24 mg/kg human equivalent dose (HED) of dexamethasone base;

vii) 15 mg/kg human equivalent dose (HED) of dexamethasone base;

viii) 24 mg/kg human equivalent dose (HED) of dexamethasone base;

ix) 30 mg/kg human equivalent dose (HED) of dexamethasone base;

x) 45 mg/kg human equivalent dose (HED) of dexamethasone base; or xi) a human equivalent dose (HED) of dexamethasone base taking a value in mg/kg from a range of mg/kg values, wherein said range is bound by two of the mg/kg values set forth in parts i) to x) above.

311. The method according to any preceding statement, wherein the glucocorticoid-receptor (GR) modulating agent is administered as a single acute dose, or as a total dose given over about a 72 hour period.

312. The method according to any preceding statement, wherein the method comprises contacting the cell with one or more further doses of a glucocorticoid-receptor (GR) modulating agent.

313. The method according to statement 313, wherein the one or more further doses are administered:

i) between 24 hours and 120 hours after a preceding administration;

ii) between 24 hours and 48 hours after a preceding administration;

iii) between 72 hours and 120 hours after a preceding administration;

iv) every 24, 48, 72, 96, 120, 144, or 168 hours after a first administration;

v) once every two weeks after a first glucocorticoid administration;

vi) once monthly after a first administration; or vii) twice weekly after a first administration.

314. The method according to any preceding statement, wherein the cell is in vitro, ex vivo, or in vivo in a subject.

315. The method according to statement 314, wherein the cell is a cancer cell.

316. The method according to statement 314 wherein the cell is a lymphocyte, monocyte, or neutrophil.

317. The method according to any one of statements 314-316, wherein the subject is mammalian, preferably wherein the subject is human.

318. The method according statement 317, wherein the subject has, is suspected of having, or has been diagnosed with cancer or a lymphocyte-mediated disease or a microbial disease.

319. The method of statement 315 or 318, wherein the cancer is a lymphoma, melanoma, or osteosarcoma.

320. The method of statement 319, wherein the cancer is lymphoma, preferably a germinal cell lymphoma, B cell lymphoma, T cell lymphoma, or non Hodgkin lymphoma.

321. The method of any preceding statement, wherein the glucocorticoid-receptor (GR) modulating agent induces cell death of ICAM3 expressing cells by binding to ICAM3.

322. The method of any preceding statement, wherein the glucocorticoid-receptor (GR) modulating agent induces apoptosis of ICAM3 expressing cells by binding to ICAM3.

323. The method according to any preceding statement, wherein the glucocorticoid-receptor (GR) modulating agent triggers (activates) cell apoptotic pathways.

324. The method according to any preceding statement, wherein the glucocorticoid-receptor (GR) modulating agent causes ICAM3 shedding from the surface of a cell into the extracellular space.

325. The method according to any preceding statement, wherein the glucocorticoid-receptor (GR) modulating agent causes ICAM3 expressing cells to be marked for attack by immune cells.

326. The method according to any preceding statement, wherein the glucocorticoid-receptor (GR) modulating agent triggers or supports an effective immune response against the ICAM3 expressing cells.

327. The method according statement 326, wherein the effective immune response involves the induction and/or mobilisation of a population of NKT cells that are characterized in that they expresses CD3, and:

i) express CD4, CD8, CD45, CD49b (CD56 in humans), CD62L, NK1.1, Ly6G, Sca1, and/or TCR gamma/delta; and/or ii) do not express: C-kit, B220, FoxP3, and/or TCR alpha/beta.

328. The method according to statement 326 or 327, wherein the effective immune response involves the induction and/or mobilisation of a population of T cells that express CD3 to a very high level ("CD3-very-high").

329. The method according to any one of statements 326-327, wherein the effective immune response involves the induction and/or mobilisation of a population of dendritic cells (DCs) that express CD11b to a very high level ("CD11b-very-high dendritic cells"). 330. The method according to any preceding statement, wherein the method of killing an ICAM3 expressing cell is a method of treating cancer or a lymphocyte-mediated disease or a microbial disease according to any one of statements 101-130.

331. A glucocorticoid-receptor (GR) modulating agent for use in a method according to any one of statements 301-330.

332. Use of a glucocorticoid-receptor (GR) modulating agent for the manufacture of a medicament for use in a method according to any one of statements 301-330.

The invention claimed is:

1. A method of treating a cancer or a microbial disease in a subject, the method comprising administering a therapeutically effective amount of a glucocorticoid to the subject, wherein the glucocorticoid induces cell death of ICAM3 expressing cells by binding to ICAM3;

wherein the cancer is an ICAM3-expressing cancer; wherein the cancer is not a lymphoma; and wherein the microbial disease is not a human immunodeficiency virus (HIV) disease.

2. The method of claim 1, wherein the glucocorticoid is selected from the group consisting of: dexamethasone, hydrocortisone, methylprednisolone, prednisone, prednisolone, prednylidene, cortisone, budesonide, betamethasone, flumethasone, ciclesonide, and beclomethasone.

3. The method according to claim 1, wherein the glucocorticoid is selected from the group consisting of: dexamethasone, betamethasone, and methylprednisone.

4. The method according to claim 1, wherein the glucocorticoid is selected from the group consisting of dexamethasone base, dexamethasone sodium phosphate, dexamethasone hemisuccinate, dexamethasone sodium succinate, dexamethasone succinate, dexamethasone isonicotinate, dexamethasone-21-acetate, dexamethasone phosphate, dexamethasone-21-phosphate, dexamethasone tebutate, dexamethasone-17-valerate, dexamethasone acetate monohydrate, dexamethasone pivalate, dexamethasone palmitate, dexamethasone-21-palmitate, dexamethasone dipropionate, dexamethasone propionate, dexamethasone acetate anhydrous, dexamethasone-21-phenylpropionate, dexamethasone-21-sulfobenzoate, dexamethasone hemo-sulfate, dexamethasone sulfate, dexamethasone beloxil, dexamethasone acid, dexamethasone acefurate, dexamethasone carboximide, dexamethasone cipecilate, dexamethasone 21-phosphate disodium salt, dexamethasone mesylate, dexamethasone linoleate, dexamethasone glucoside, dexamethasone glucuronide, dexamethasone iodoacetate, dexamethasone oxetanone, carboxymethylthio-dexamethasone, dexamethasonebisethoximes, dexamethasone epoxide, dexamethasonelinolelaidate, dexamethasone methylorthovalerate, dexamethasone spermine, 6-hydroxy dexamethasone, dexamethasone tributylacetate, dexamethasone aspartic acid, dexamethasone galactopyranose, dexamethasone hydrochloride, hydroxy dexamethasone, carboxy dexamethasone, desoxy dexamethasone, dexamethasone butazone, dexamethasone cyclodextrin, dihydro dexamethasone, oxo dexamethasone, propionyloxy dexamethasone, dexamethasone galactodie, dexamethasone isonicotinate, dexamethasone sodium hydrogen phosphate, dexamethasone aldehyde, dexamethasone pivlate, dexamethasone tridecylate, dexamethasone crotonate, dexamethasone methanesulfonate, dexamethasone butylacetate, dehydro dexamethasone, dexamethasone Isothiocyanatoethyl) Thioether, dexamethasone bromoacetate, dexamethasone hemiglutarate, deoxy dexamethasone, dexamethasone chlorambucilate, dexamethasone melphalanate, formyloxy dexamethasone, dexamethasone butyrate, dexamethasone laurate, dexamethasone acetate, and any combination treatment that contains a form of dexamethasone.

5. The method according to claim 1, wherein the glucocorticoid is administered at a dose equivalent to about:

6-45 mg/kg human equivalent dose (HED) of dexamethasone base.

6. The method according to claim 1, wherein the glucocorticoid is administered as a single acute dose, or as a total dose given over about a 72 hour period.

7. The method according to claim 1, wherein the method comprises administering one or more further doses of a glucocorticoid to the subject.

8. The method according to claim 7, wherein the one or more further doses are administered:

i) between 24 hours and 120 hours after a preceding administration;

ii) every 24, 48, 72, 96, 120, 144, or 168 hours after a first administration;

iii) once every two weeks after a first glucocorticoid administration;

iv) once monthly after a first administration; or v) twice weekly after a first administration.

9. The method according to claim 1, wherein the subject has, is suspected of having, or has been diagnosed with an ICAM3-expressing cancer or a non-human immunodeficiency virus (HIV) microbial disease.

10. The method of claim 1, wherein the cancer is a melanoma or an osteosarcoma.

11. The method of claim 1, wherein the glucocorticoid induces apoptosis of ICAM3 expressing cells by binding to ICAM3.

12. The method of claim 1, wherein the glucocorticoid causes ICAM3 shedding from the surface of a cell into the extracellular space.

13. The method according to claim 1, wherein the glucocorticoid causes ICAM3 expressing cells to be marked for attack by immune cells.

14. The method according to claim 1, wherein the glucocorticoid triggers or supports an effective immune response against an ICAM3 expressing cancer cell.

15. The method according to claim 14, wherein the effective immune response involves the induction and/or mobilisation of a population of NKT cells that express CD3, and:

i) express CD4, CD8, CD45, CD49b, CD62L, NK1.1, Ly6G, Sca1, and/or TCR gamma/delta; and/or ii) do not express: C-kit, B220, FoxP3, and/or TCR alpha/beta.

16. The method according to claim 14, wherein the effective immune response involves the induction and/or mobilisation of a population of T cells that express CD3 to a very high level ("CD3-very-high").

17. The method according to claim 14, wherein the effective immune response involves the induction and/or mobilisation of a population of dendritic cells (DCs) that express CD11b to a very high level ("CD11b-very-high dendritic cells").

* * * * *